US 7,583,993 B2

(12) United States Patent
Sendai

(10) Patent No.: US 7,583,993 B2
(45) Date of Patent: *Sep. 1, 2009

(54) FLUORESCENCE IMAGE DISPLAY APPARATUS

(75) Inventor: Tomonari Sendai, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 288 days.

This patent is subject to a terminal disclaimer.

(21) Appl. No.: 11/250,510

(22) Filed: Oct. 17, 2005

(65) Prior Publication Data

US 2006/0058684 A1    Mar. 16, 2006

Related U.S. Application Data

(63) Continuation of application No. 10/138,527, filed on May 6, 2002, now Pat. No. 7,043,291.

(30) Foreign Application Priority Data

May 7, 2001   (JP)   ............................. 2001/136046
Mar. 27, 2002 (JP)   ............................. 2002/089108

(51) Int. Cl.
    *A61B 6/00* (2006.01)
(52) U.S. Cl. ...................................... 600/476; 600/473
(58) Field of Classification Search ................. 600/476, 600/473; 382/167–168, 274, 162–163
    See application file for complete search history.

(56) References Cited

U.S. PATENT DOCUMENTS

| 4,805,016 | A | * | 2/1989 | Kato ........................... 348/71 |
| 5,386,819 | A | | 2/1995 | Kaneko et al. |
| 5,436,661 | A | | 7/1995 | Yamamoto et al. |
| 5,515,449 | A | | 5/1996 | Tsuruoka et al. |
| 5,566,673 | A | | 10/1996 | Shiono et al. |
| 5,647,368 | A | | 7/1997 | Zeng et al. |
| 5,749,830 | A | | 5/1998 | Kaneko et al. |
| 5,833,617 | A | | 11/1998 | Hayashi |
| 5,986,271 | A | | 11/1999 | Lazarev et al. |
| 6,059,720 | A | | 5/2000 | Furusawa et al. |
| 6,110,106 | A | | 8/2000 | MacKinnon et al. |
| 6,556,853 | B1 | | 4/2003 | Cabib et al. |
| 6,574,502 | B2 | | 6/2003 | Hayashi |
| 6,826,424 | B1 | | 11/2004 | Zeng et al. |

FOREIGN PATENT DOCUMENTS

| JP | 2001-157658 | 2/2001 |
| WO | WO 02/07587 A2 | 1/2002 |

* cited by examiner

*Primary Examiner*—Brian Casler
*Assistant Examiner*—Peter Luong
(74) *Attorney, Agent, or Firm*—Sughrue Mion, PLLC

(57) ABSTRACT

A fluorescence image display apparatus is provided; wherein, when a pseudo color image representing the tissue state of a target subject is obtained, based on a fluorescence image emitted from the target subject upon the irradiation thereof by an excitation light, the tissue state can be recognized regardless of the intensity of the fluorescent light. Based upon the statistical quantity of a wide band fluorescence image computed by a statistical quantity computing means, a gain that the wide band and narrow band fluorescence image data are to be multiplied by is computed by a gain computing means. A gain multiplying means multiplies the wide band and narrow band fluorescence image data by the gain, whereby a green gradation is assigned to the wide band fluorescence image and a red gradation is assigned to the narrow band fluorescence image, and a composite image data is obtained by an image composing means.

9 Claims, 24 Drawing Sheets

FLUORESCENCE IMAGE DISPLAY APPARATUS

This is a Continuation of application Ser. No. 10/138,527 filed May 6, 2002. The entire disclosure of the prior application Ser. No. 10/138,527 is hereby incorporated by reference.

BACKGROUND OF THE INVENTION

1. Field of the Invention

The present invention relates in general to a fluorescence image display apparatus, and in particular to a fluorescence image display apparatus for measuring the fluorescent light emitted from a target subject upon the irradiation thereof by an excitation light and displaying as an image the data relating to said target subject.

2. Description of the Related Art

Fluorescent light detection apparatuses have been proposed that make use of the fact that the intensity of the fluorescent light emitted from a normal tissue differs from the intensity of the fluorescent light emitted from a diseased tissue when a target subject (i.e., a living tissue) is irradiated by an excitation light within an excitation wavelength range of the intrinsic fluorophores of the target subject, wherein, by detecting the fluorescent light emitted from a target subject upon irradiation thereof by an excitation light within a predetermined wavelength range, the location and range of penetration of a diseased tissue is discerned.

Normally, when a target subject is irradiated by an excitation light, because a high-intensity fluorescent light is emitted from a normal tissue, as shown by the solid line in FIG. 26, and a weak-intensity fluorescent light is emitted from a diseased tissue, as shown by the broken line in FIG. 26, by measuring the intensity of the fluorescent light emitted from the target subject, it can be determined whether the target subject is in a normal or a diseased state. These types of fluorescence image display apparatuses are in many cases provided built in to the configuration of an endoscope for insertion into a body cavity of a patient, a colposcope, or a surgical microscope.

However, for cases in which the intensity of the fluorescent light emitted from a target subject upon the irradiation thereof by the excitation light is to be displayed as an image, because there is unevenness on the surface of a target subject, the intensity of the excitation light irradiating the target subject is not of a uniform intensity. Further, although the intensity of the fluorescent-light emitted from the target subject is substantially proportional to the intensity of the excitation light, the intensity of the aforementioned excitation light becomes weaker in inverse proportion to the square of the distance between the excitation light and the target subject. Therefore, there are cases in which the fluorescent-light received from a diseased tissue located at a position closer to the excitation light source than a normal tissue is of a higher intensity than the fluorescent-light received from aforementioned normal tissue, and the state of the tissue of the target subject cannot be accurately discerned based solely on the data relating to the intensity of the fluorescent-light received from the target subject upon the irradiation thereof with an excitation light.

In order to remedy the problems described above, methods such as that described in the specification of U.S. Pat. No. 5,647,368, wherein by colorizing and synthesizing a fluorescence image obtained by irradiating a target subject with an excitation light having a wavelength in the wavelength range near 500 nm, upon which the intensity of the fluorescent light emitted from the target subject changes by a large degree depending on the tissue state of the target subject, with a fluorescence image obtained by irradiating the target subject with an excitation light having a frequency in the wavelength range near 630 nm, upon which the intensity of the fluorescent light emitted from the target subject exhibits no change depending on the tissue state of the target subject, to obtain a colorized synthesized image; when said colorized synthesized image is displayed, the tissue state of the target subject can be accurately discerned based on the visually recognizable color thereof, have been proposed.

Further, there has been proposed, as described in Japanese Unexamined Patent Publication No. 2001-157658 (not patented), a method of colorizing and displaying two types of fluorescence images based on the irradiation of a target subject with two different wavelengths of excitation light (a narrow band excitation light having a wavelength near 480 nm, and a wide band excitation light having a wavelength within the wide band of 430-730 nm). According to this method, because the band of the fluorescent light is wider in comparison to the method proposed in the aforementioned U.S. Pat. No. 5,647,368, the S/N ratio of the images obtained by additive color mixture can be improved, and because the intensity of the fluorescence images changes by a large amount in accordance with the tissue state of the target subject for both bands, the color change corresponding to the change in the tissue state can be made more distinct, whereby the distinguishability of the tissue state is improved a level.

However, according to the above described methods of displaying colorized synthesized images, the color of the image to be displayed is regulated by a chromaticity, which is determined in correspondence to the of the ratio of the two types of fluorescence images that are to be color added and mixed, and a luminosity, which is determined in correspondence to the intensity of the fluorescence images. Because the chromaticity of the image to be displayed is determined in correspondence to the ratio of the two types of fluorescence images that are to be color added and mixed, the chromaticity of the image that is to be displayed, which corresponds to the tissue state of the target subject, can be determined at once. However, because the fluorescent light intensity differs according to the distance between the light source and the target subject, the luminosity of the image to be colorized differs according to the aforementioned distance. Here, these types of fluorescence image display apparatuses are in many cases provided in the configuration of an endoscope for insertion into a body cavity of a patient, a colposcope, or a surgical microscope; because the objective of the use thereof is the measurement of an internal portion of a body cavity, the distance between the target subject and any of said apparatuses is between several to 50 mm. Therefore, if the distance between the distal end of the insertion portion that is inserted into the body cavity of a patient and the target subject changes, the intensity of the fluorescent light changes; as a result, the luminosity of the synthesized image changes. If the luminosity of the colorized synthesized image changes in this manner, because the color appearing in the displayed color added and mixed image will be recognized as a different color even if the chromaticity thereof is the same, there is a fear that even though tissues have the same tissue state, said tissues will be discerned to have different tissue states. On the other hand, for cases in which the luminosity of the image to be colorized is low, there are cases in which even though a chromaticity is different, the color in the displayed colorized synthesized image cannot be recognized to be different, giving rise to a fear that a diseased portion might be overlooked.

SUMMARY OF THE INVENTION

The present invention has been developed in consideration of the forgoing circumstances, and it is an object of the present invention to provide a fluorescence image display apparatus capable of displaying a fluorescence image wherein it is possible to accurately discern, regardless of the intensity of the fluorescent light, the tissue state of the target subject depicted therein.

The first fluorescence image display apparatus according to the present invention comprises a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a gain computing means for computing, based on the statistical quantity of either one of said two fluorescence image data, a gain that said two fluorescence image data are to be multiplied by, a multiplying means for multiplying said two fluorescence image data by said gain and obtaining two multiplied fluorescence image data, an image forming means for forming, based on said two multiplied fluorescence image data, a pseudo color image data representing a pseudo color image reflecting the tissue state of the target subject, and an image display means for displaying said pseudo color image.

Here, the expression "based on the statistical quantity of either one of said two fluorescence image data, a gain that said two fluorescence image data are to be multiplied by" refers to, for example: in a case in which the statistical quantity of the fluorescence image data is smaller than a desired value, that is, when the size of the data value of the fluorescence image data is not large enough, the a gain is computed so that the data value of the multiplied fluorescence image data becomes a larger value than that of the fluorescence image data, whereby the statistical quantity of the multiplied fluorescence image data becomes greater than or equal to the aforementioned desired value; for a case in which the statistical quantity of the fluorescence image data is larger than a desired value, that is, when the size of the data value of the fluorescence image data is too large, a gain is computed so that the data value of the multiplied fluorescence image data becomes a smaller value than that of the fluorescence image data, whereby the statistical quantity of the multiplied fluorescence image data becomes less than or equal to the aforementioned desired value; and, for a case in which the statistical quantity of the fluorescence image data is substantially equivalent to a desired value, that is, when the size of the data value of the fluorescence image data is adequately large, a gain is computed so that the data value of the multiplied fluorescence image data becomes substantially equivalent to that of the fluorescence image data.

More specifically, the gain can be computed by use of the following formulas (1) or (2). That is to say, if the dynamic range of the display means is designated as DR (e.g., 255 in the case of data formed of eight bits), the largest value of the fluorescence image data as Max, the smallest value of the fluorescence image data as Min, and two arbitrary constants a (0.9-0.95), and b (e.g., 2) are designated:

$$\text{Gain upper limit} = DR \times a / \{(Max+Min)/2 + b \times (Max-Min)/2\} \quad (1)$$

Further, if the dynamic range of the display means is designated as DR, the average value of the fluorescence image data as m, the standard deviation as σ, and two arbitrary constants a and b are designated:

$$\text{Gain lower limit} = DR \times a / (m + b \times \sigma) \quad (2)$$

Note that if the gains that the two fluorescence image data are to be multiplied by have a constant relationship (e.g., making the gain that one of the two fluorescence image data is multiplied by C times that which the other of the two fluorescence image data is multiplied by {where C is a constant} etc.) the gains can be of different values.

Note that according to the first fluorescence image display apparatus of the present invention, the image forming means can also be a means for forming the pseudo color image, based on the additive color mixture method, from both of the multiplied fluorescence image data.

Further, according to the first fluorescence image display apparatus of the present invention, the image forming means can be a means comprising: a color image forming means for forming a color added and mixed image data, based on the additive color mixture method, from both of the multiplied fluorescence image data, and a color image data, based on said color added and mixed image data, representing the chromatic components of the color added and mixed image represented by said data, a luminosity image forming means for forming a luminosity image data representing a luminosity image by assigning a luminosity display gradation to the pixel values of the multiplied fluorescence image represented by either of the two multiplied fluorescence image data, and a composite image forming means for combining the color image data and the luminosity image data to form a composite image.

The referents of "chromatic components" include all of the following: the hue of the color added and mixed image; the color saturation, or the color saturation and the hue; the X,Y components of an XYZ color space; the ab components of a Lab color space; the uv components of a Luv color space; the a*b* components of a uniform La*b* color space; the u*v* components of a uniform Lu*v* color space; etc.

The expression "assigning a luminosity display gradation to the pixel values of the multiplied fluorescence image represented by either of the two multiplied fluorescence image data" refers to the assignment of a numerical value representing a degree of brightness to each pixel value of the multiplied fluorescence image, corresponding to the size of each said pixel value.

Further, the image forming means can be a means comprising: a color image forming means for forming a color added and mixed image data, based on the additive color mixture method, from both of the multiplied fluorescence image data, and a color image data, based on said color added and mixed image data, representing the chromatic components of the color added and mixed image represented by said color added and mixed image data, a luminosity image forming means for forming a luminosity image data representing a luminosity image by assigning a luminosity display gradation to the pixel values of the fluorescence image represented by either of the two fluorescence image data, and a composite image forming means for combining the color image data and the luminosity image data to form a composite image.

Further, the first fluorescence image display apparatus according to the present invention can further comprise a dynamic range expanding means for expanding, based on the statistical quantity, the dynamic range of both of the multiplied fluorescence image data so that the dynamic range thereof spans substantially the entirety of the dynamic range of the display region of display means.

In this case, it is preferable that a switching means for switching between a drive mode and a non-drive mode of the dynamic range expanding means be further provided.

Further, according to the first fluorescence image display apparatus of the present invention, the gain computing means can be a means for computing the gain based on the statistical quantity of a desired region of the fluorescence image represented by either of the fluorescence image data.

Here, the referent of "a desired region" is, for example, an image region of an obtained fluorescence image that is an area with a high level of interest.

Further, according to the first fluorescence image display apparatus of the present invention, it is preferable that the statistical quantity be formed of at least one of the following: the maximum value of the fluorescence image data, the minimum value of the fluorescence image data, the average value of the fluorescence image data, a value combining the maximum value of the fluorescence image data and the standard deviation, a value combining the maximum and minimum values of the fluorescence image data, a value combining the minimum value of the fluorescence image data and the standard deviation, and a value combining the average value of the fluorescence image data and the standard deviation.

The second fluorescence image display apparatus according to the present invention comprises: a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on the statistical quantity of said reflectance image data, a gain that said two fluorescence image data are to be multiplied by, a multiplying means for multiplying said two fluorescence image data by said gain and obtaining two multiplied fluorescence image data, an image forming means for forming, based on said two multiplied fluorescence image data, a pseudo color image data representing a pseudo color image reflecting the tissue state of the target subject, and an image display means for displaying said pseudo color image.

Note that according to the second fluorescence image display apparatus of the present invention, the image forming means can also be a means for forming the pseudo color image, based on the additive color mixture method, from both of the multiplied fluorescence image data.

Further, according to the second fluorescence image display apparatus of the present invention, the image forming means can be a means comprising: a color image forming means for forming a color added and mixed image data, based on the additive color mixture method, from both of the multiplied fluorescence image data, and a color image data, based on said color added and mixed image data, representing the chromatic components of the color added and mixed image represented by said color added and mixed image data, a luminosity image forming means for obtaining a multiplied reflectance image data by multiplying the reflectance image data by said gain, and forming a luminosity image data representing a luminosity image by assigning a luminosity display gradation to the pixel values of the multiplied reflectance image or the pixel values of the multiplied fluorescence image represented by either of the two multiplied fluorescence image data, and a composite image forming means for combining the color image data and the luminosity image data to form a composite image.

In this case, it is preferable that it be possible to switch the image to which the luminosity display gradation is to be assigned between the multiplied reflectance image and either of the two multiplied fluorescence images.

It is preferable that a light that is not readily absorbable by the target subject, such as near-infrared light or the like be used as the reference light.

Further, the image forming means can be a means comprising: a color image forming means for forming a color added and mixed image data, based on the additive color mixture method, from both of the multiplied fluorescence image data, and a color image data, based on said color added and mixed image data, representing the chromatic components of the color added and mixed image represented by said color added and mixed image data, a luminosity image for forming means forming a luminosity image data representing a luminosity image by assigning a luminosity display gradation to the pixel values of the reflectance image or the pixel values of the fluorescence image represented by either of the two fluorescence image data, and a composite image forming means for combining the color image data and the luminosity image data to form a composite image.

In this case also, it is preferable that it be possible to switch the image to which the luminosity display gradation is to be assigned between the multiplied reflectance image and either of the two multiplied fluorescence images.

The third fluorescence image display apparatus according to the present invention comprises: a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on the statistical quantity of said reflectance image data, a gain that said two fluorescence image data are to be multiplied by, a multiplying means for multiplying said two fluorescence image data by said gain and the reflectance image data to obtain two multiplied fluorescence image data and a multiplied reflectance data, a difference computing means for computing the difference data between the multiplied reflectance image data and either of the two multiplied fluorescence image data, an image forming means for forming, based on said difference data and the other multiplied fluorescence image data of the aforementioned two multiplied fluorescence image data, a pseudo color image data representing a pseudo color image reflecting the tissue state of the target subject, and an image display means for displaying said pseudo color image.

Note that according to the third fluorescence image display apparatus of the present invention, the image forming means can also be a means for forming the pseudo color image, based on the additive color mixture method, from both of the multiplied fluorescence image data.

Further, according to the third fluorescence image display apparatus of the present invention, the image forming means can be a means comprising: a color image forming means for forming a color added and mixed image data, based on the additive color mixture method, from the difference data and the multiplied fluorescence image data, and a color image data, based on said color added and mixed image data, representing the chromatic components of the color added and mixed image represented by said color added and mixed image data, a luminosity image forming means for assigning a luminosity display gradation to the pixel values of the multiplied reflectance image represented by the multiplied reflectance image data or the pixel values of the multiplied fluorescence image represented by either of the two multiplied fluorescence image data to form a luminosity image data representing a luminosity image, and a composite image forming means for combining the color image data and the luminosity image data to form a composite image.

In this case, it is preferable that it be possible to switch the image to which the luminosity display gradation is to be assigned between the multiplied reflectance image and either of the two multiplied fluorescence images.

Further, according to the third fluorescence image display apparatus of the present invention, the image forming means can be a means comprising: a color image forming means for forming a color added and mixed image data, based on the additive color mixture method, from both of the multiplied fluorescence image data, and a color image data, based on said color added and mixed image data, representing the chromatic components of the color added and mixed image represented by said color added and mixed image data, a luminosity image forming means for assigning a luminosity display gradation to the pixel values of the reflectance image represented by the multiplied reflectance image data or the pixel values of the fluorescence image represented by either of the two fluorescence image data to form a luminosity image data representing a luminosity image, and a composite image forming means for combining the color image data and the luminosity image data to form a composite image.

In this case also, it is preferable that it be possible to switch the image to which the luminosity display gradation is to be assigned between the multiplied reflectance image and either of the two multiplied fluorescence images.

Further, the second and third fluorescence image display apparatuses according to the present invention may further comprise a dynamic range expanding means for expanding, based on the statistical quantity, the dynamic range of the reflectance image data and/or both of the multiplied fluorescence image data so that the dynamic range thereof spans substantially the entirety of the display means.

In this case, it is preferable that a switching means for switching between a drive mode and a non-drive mode of the dynamic range expanding means be further provided.

Further, according to the second and third fluorescence image display apparatuses of the present invention, the gain computing means can be a means for computing the gain based on the statistical quantity of a desired region of the reflectance image represented by the reflectance image data.

Further, according to the second and third fluorescence image display apparatuses of the present invention, it is preferable that the statistical quantity be formed of at least one of the following: the maximum value of the fluorescence image data, the minimum value of the fluorescence image data, the average value of the fluorescence image data, a value combining the maximum value of the fluorescence image data and the standard deviation, a value combining the maximum and minimum values of the fluorescence image data, a value combining the minimum value of the fluorescence image data and the standard deviation, and a value combining the average value of the fluorescence image data and the standard deviation.

Note that according to the first through third fluorescence image display apparatuses of the present invention: the image forming means can be a means for obtaining a reverse fluorescence image data by inverting the light intensity of either of the multiplied fluorescence image data; and forming a pseudo color image, based on this reverse fluorescence image data and the other multiplied fluorescence image data of the aforementioned two multiplied fluorescence image data.

The expression "obtaining a reverse fluorescence image data by inverting the light intensity of either of the multiplied fluorescence image data" refers to the subtraction of the pixel value of each pixel of the multiplied fluorescence image represented by a multiplied fluorescence image data from the largest obtainable value of the multiplied fluorescence image data (e.g., if the data consists of 8 bits, 255), or the computation of the reciprocal value of the pixel value of each pixel.

Further, according to the first through third fluorescence image display apparatuses of the present invention: the image forming means can be a means for obtaining a reverse fluorescence image data by inverting the light intensity of either of the multiplied fluorescence image data; multiplying the reverse fluorescence image data by a predetermined constant to obtain a constant-multiplied reverse fluorescence image data and forming the pseudo color image based on this constant-multiplied reverse fluorescence image data and the other multiplied fluorescence image data of the aforementioned two multiplied fluorescence image data.

A value less than 1 can be used as the constant.

Note that according to the first through third fluorescence image display apparatuses of the present invention: for cases in which the fluorescence image data or the reflectance image data is represented by data constituted of 9 bits or more, a bit shifting means can be provided for shifting the bits of the fluorescence image data or the reflectance image data so that said data is expressed by the lower 8 bits thereof, and the statistical quantity computing means can be a means for computing the statistical quantity based on the bit-shifted data; and the gain computing means can be a means for computing the gain based on the statistical quantity of the bit shifted data value.

Here, the expression "shifting the bits of the fluorescence image data or the reflectance image data so that said data is expressed by the lower 8 bits thereof" refers to the rounding off of the bit data in the case that the fluorescence image data is expressed by 9 or more bits so as to obtain a data value of less than 8 bits; 8-bit data can be computed by use of a common calculator.

Further, a portion or the entirety of the fluorescence image obtaining means of the first fluorescence image display apparatus or of the fluorescence image obtaining means and reflectance image obtaining means of the second and third fluorescence image obtaining apparatuses according to the present invention can be provided in the form of an endoscope provided with an insertion portion to be inserted into a body cavity of a patient.

Here, the expression "provided in the form of an endoscope" refers to the disposal of a portion or the entirety of the fluorescence image obtaining means and the reflectance image obtaining means within the interior portion of an endoscope system. Further, the referents of "a portion" include the light emitting end for emitting the excitation light and the reference light, and the light receiving end for receiving the fluorescent light emitted from the target subject upon the irradiation thereof by the excitation light and the reference light reflected from the target subject upon the irradiation thereof by the reference light.

Further, the excitation light source may be a GaN type semiconductor laser, and the wavelength band thereof can be in the 400-420 nm range.

Note that the first through third fluorescence image display apparatuses according to the present invention may also be provided as apparatuses combining the additional function of obtaining and displaying a standard image, based on the light reflected from the target subject upon the irradiation thereof by a white light.

According to the first fluorescence image display apparatus of the present invention: a gain that two fluorescence image data are to be multiplied by is computed based on the statistical quantity of either of two fluorescence image data; two multiplied fluorescence image data are obtained by multiplying both of the fluorescence image data by this gain; and a pseudo color image data representing a pseudo color image reflecting the tissue state of the target subject is obtained based on both of the multiplied fluorescence image data. Therefore, because a pseudo color image can be obtained from a multiplied fluorescence image data having a desired data value, the pseudo color image can be formed so as to have a desired luminosity, regardless of the intensity of the fluorescent light. That is to say, the luminosity of the fluorescence image, which is an effect of the intensity of the fluorescent light, can be adjusted so as to be within a desired luminosity range, whereby the distinguishability of the tissue state of the target subject can be improved.

According to the second fluorescence image display apparatus of the present invention: a gain that two fluorescence image data are to be multiplied by is computed based on the statistical quantity of the reflectance image data representing a reflectance image formed of the light reflected from a target subject upon the irradiation thereof by a reference light; two multiplied fluorescence image data are obtained by multiplying both of the fluorescence image data by this gain; and a pseudo color image data representing a pseudo color image reflecting the tissue state of the target subject is obtained based on both of the multiplied fluorescence image data. Therefore, because a pseudo color image can be obtained from a multiplied fluorescence image data having a desired data value, the pseudo color image can be formed so as to have a desired luminosity, regardless of the intensity of the fluorescent light. That is to say, the luminosity of the fluorescence image, which is an effect of the intensity of the fluorescent light, can be adjusted so as to be within a desired range, whereby the distinguishability of the tissue state of the target subject can be improved. Further, because the intensity of said reflectance image is higher than that of the fluorescence image, the computation of the gain, which is performed based on the statistical quantity, can be performed more adequately.

According to the third fluorescence image display apparatus of the present invention: a gain that two fluorescence image data are to be multiplied by is computed based on the statistical quantity of the reflectance image data representing a reflectance image formed of the light reflected from a target subject upon the irradiation thereof by a reference light; a multiplied reflectance image data and two multiplied fluorescence image data are obtained, respectively, by multiplying the reflectance image data and both of the fluorescence image data by this gain; the difference data between the multiplied reflectance image and either of the two multiplied fluorescence images is computed; and a pseudo color image data representing a pseudo color image reflecting the tissue state of the target subject is obtained based on the difference data and the other multiplied fluorescence image data of the aforementioned two multiplied fluorescence image data. Therefore, because a pseudo color image can be obtained from a multiplied fluorescence image data having a predetermined data value, the pseudo color image can be formed so as to have a desired luminosity, regardless of the intensity of the fluorescent light. Further, by computing the difference data between the multiplied reflectance image and the multiplied fluorescence image, the difference between the diseased tissue and the normal tissue can be more clearly rendered. That is to say, by adjusting the luminosity of the fluorescence image, which is an effect of the intensity of the fluorescent light, to within a desired luminosity range, the distinguishability of the tissue state of the target subject can be improved.

Further, by forming, based on the additive color mixture method, a pseudo color image data from both of the multiplied fluorescence image data, the tissue state of the target subject can be accurately discerned based on the visually recognized color.

Still further: by forming, based on the additive color mixture method, a pseudo color image data from both of the multiplied fluorescence image data, and a color image data, based on said color added and mixed image data, representing the chromatic components of the color added and mixed image represented by said color added and mixed image data; assigning a luminosity display gradation to the pixel values of the multiplied reflectance image or the pixel values of either of the two multiplied fluorescence images to form a luminosity image data; and combining the color image data and the luminosity image data to form a composite image; the hue of the displayed pseudo color image becomes a hue reflecting the tissue state of the target subject; the luminosity reflects the light intensity for cases in which the multiplied reflectance image has been employed to form the luminosity image data, that is, the form of the target subject; and for cases in which the one of the multiplied fluorescence image has been employed to form the luminosity image data, the luminosity reflects the tissue state of the target subject in addition to the form thereof. Accordingly, data relating to the tissue state of the target subject as well as data relating to the form of the target subject can be displayed concurrently in a single image. In particular, for cases in which the luminosity image data has been formed from one of the multiplied fluorescence images, even for cases in which the distance between the target subject and the light emitting end of the excitation light source is comparatively small, if there is a diseased portion present in said target subject, because the luminosity thereof is reduced, the luminosity contrast can be added to the chromaticity contrast in the pseudo color image.

Note that for cases in which a luminosity display gradation is assigned to the multiplied reflectance image or either of the two multiplied fluorescence images, because the gain changes by a large amount if the distance between the target subject and the image obtaining means changes a large amount, the brightness of the displayed pseudo color image also changes by a corresponding large amount. Therefore, by assigning a luminosity display gradation to the reflectance image or either of the two fluorescence images prior to the multiplication of the gain therewith, a large change in the brightness of the pseudo color image can be prevented.

Further, by expanding the dynamic range of the multiplied reflectance image data and/or the dynamic range of both of the multiplied fluorescence image data, so that the dynamic range of the multiplied reflectance image data and/or the dynamic range of both of the multiplied fluorescence image data spans substantially the entire dynamic range of the display means, because the contrast of the multiplied reflectance image or the multiplied fluorescence image can be expanded, the change in the tissue state of the target subject appearing in the pseudo color image can be represented in detail, whereby the distinguishability of the tissue state of the target subject can be improved.

Note that in this case, by switching, by use of a switching means, the dynamic range expanding means between a drive mode and a non-drive mode, because the dynamic range expansion process can be set so as to not be performed in cases in which said process is not required, a pseudo color image reflecting the preferences of the operator can be displayed.

Further, by making the statistical quantity consist of at least one of the following elements of the fluorescence image data or the reflectance image data: the maximum value, the minimum value, the average value, a value combining the maximum value and the standard deviation, a value combining the maximum and minimum values, a value combining the minimum value and the standard deviation, and a value combining the average value and the standard deviation; the computation of the statistical quantity can be performed comparatively easily.

Still further, if the gain computing means is a means for computing the gain based on the statistical quantity of the fluorescence image data or the reflectance image data within a desired portion of the fluorescence image data or the reflectance image data, the amount of computation required for computing the statistical quantity can be reduced.

In addition, although the change in the intensity of the fluorescent light emitted from a diseased portion is in-phase in both multiplied fluorescence image data, by obtaining a reverse fluorescent image data by inverting the intensity of either of the two multiplied fluorescence image data, the change in intensity between the reverse fluorescence image data and the other of the two multiplied fluorescence image data, can be made to be antiphase. Accordingly, the change between the hue of the diseased portion and the hue of the normal portion appearing in the pseudo color image can be enlarged, whereby the distinguishability of the tissue state of the target subject can be improved a level.

Note that for cases in which the intensity has been inverted, there are cases in which the dark portions other that the diseased portion included in the pseudo color image become the same color as the diseased portion. Therefor, by multiplying the multiplied fluorescent image of which the intensity has been inverted by a constant, the effect whereby the dark portions appearing in the pseudo color image become the same color as the diseased portion can be suppressed, whereby the misrecognition of the diseased portion and the portions that are simply dark portions can be prevented, and the distinguishability of the tissue state of the target subject can be improved a level.

Further, in the case that a bit shifting means is provided for shifting the bits of the reflectance image data or the fluorescence image data for cases in which the fluorescence image data or the reflectance data is represented by data constituted of 9 bits or more, so that said data is expressed by the lower 8 bits thereof, and the gain computing means is a means for computing the gain based on the statistical quantity of the bit-shifted data, a common 8-bit calculator can be employed and the processing speed can be increased.

Still further, if a GaN type semiconductor laser is employed as the excitation light source, the light source can be provided as a compact and low-cost light source; further, if the wavelength band thereof is in the range from 400-420 nm, the fluorescent light can be caused to be generated efficiently.

DESCRIPTION OF THE PREFERRED EMBODIMENTS

Figure 1:
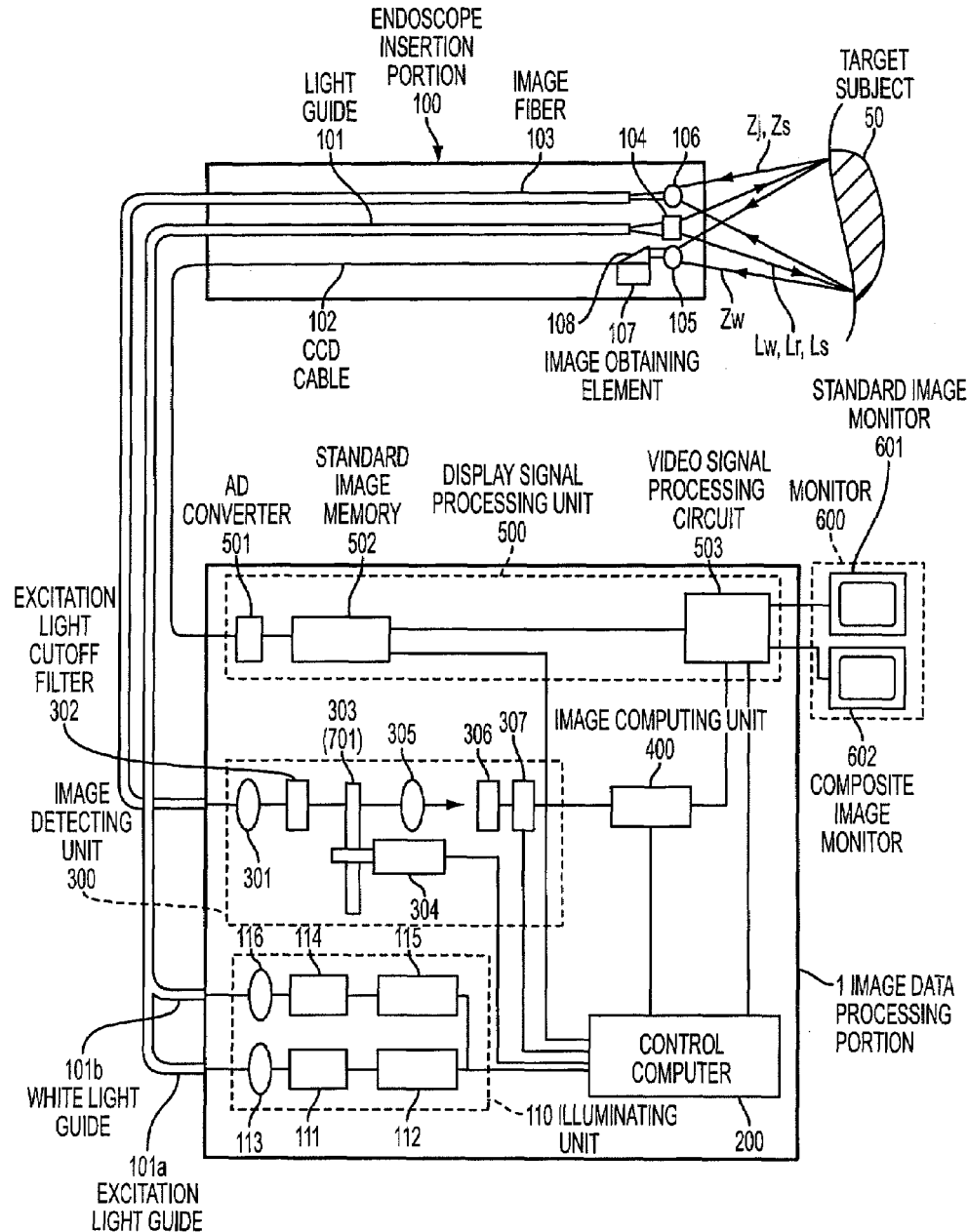
FIG. 1 is a schematic drawing of the first embodiment of a fluorescent endoscope implementing the fluorescence image display apparatus according to the present invention.

Hereinafter the preferred embodiments of the present invention will be explained with reference to the attached drawings. FIG. 1 is a schematic drawing a fluorescent endoscope implementing the fluorescence image display apparatus according to first embodiment of present invention.

The fluorescent endoscope according to the first embodiment comprises: an endoscope insertion portion 100 to be inserted into the primary nidus and areas of suspected secondary infection of a patient; an image data processing portion 1 for outputting as image data the data obtained of a living tissue (hereinafter referred to as a target subject); and a monitor 600 for displaying the image data outputted from the image data processing portion 1 as a visible image.

The image data processing portion 1 comprises: an illuminating unit 110 provided with two light sources for emitting a white light Lw for obtaining a standard image (a reflectance image) and an excitation light Lr for obtaining a fluorescence image, respectively; an image detecting unit 300 for obtaining a fluorescence image Zj, which is formed of the fluorescent light emitted from a target subject 50 upon the irradiation thereof by the excitation light Lr, and a reflectance image Zs, which is formed of the light reflected from the target subject 50 upon the irradiation thereof by the white light Lw containing a reference light Ls, and converting said obtained fluorescence image Zj and reflectance image Zs to respective digital values and outputting said digital values as respective image data; an image computing unit 400 for subjecting the image data of the fluorescence image outputted from the image detecting unit 300 to computational processes and outputting a pseudo color image data; a display signal processing unit 500 for converting a standard image to digital values to obtain an image data thereof, and converting said image data and the pseudo color image data outputted from the image computing unit 400 to video signals and outputting said video signals; and a control computer 200 for controlling the operation of each unit. Note that according to the first embodiment, the obtainment of a reflectance image Zs is not performed.

The endoscope insertion portion 100 is provided with a light guide 101 extending internally to the distal end thereof, a CCD cable 102, and an image fiber 103. An illuminating lens 104 and an objective lens 105 are provided at the distal end portion of the light guide 101 and the CCD cable 102, that is, at the distal end of the endoscope insertion portion 100. Further, the image fiber 103 is formed of a composite glass fiber, and a focusing lens 106 is provided at the distal end portion thereof. A standard image obtaining element 107 is connected to the distal end portion of the CCD cable 102, and a reflective prism 108 is attached to the standard image obtaining element 107. The light guide 101 consists of a bundled excitation light guide 101a, which is formed of quartz glass fiber, and white light guide 101b, which is formed of composite glass fiber, in the form of an integrated cable; the excitation light guide 101a and the white light guide 101b are connected to the illuminating unit 110. One end of the CCD cable 102 is connected to the image signal processing unit 500, and one end of the image fiber 103 is connected to the image detecting unit 300. Note that although not shown in the drawing, the distal end portion of the light guide 101 is formed as two eyelets.

The illuminating unit 110 comprises: a GaN type semiconductor laser 111 that emits an excitation light Lr for obtaining fluorescence images; a semiconductor laser power source 112 electrically connected to the GaN type semiconductor laser 111; an excitation light focusing lens 113 for focusing the excitation light emitted from the GaN type semiconductor laser 111; a white light source 114 that emits a white light Lw for obtaining standard images; a white light source power source 115 electrically connected to the white light source 114; and a white light focusing lens 116 for focusing the white light emitted from the white light source 114. Further, because the white light Lw emitted from the white light source 114 contains light within the wavelength band that can be used as the reference light Ls, the white light source 114 can also be employed as the reference light source described below.

The image detecting unit 300 comprises: a collimator lens 301 that focuses a fluorescence image conveyed thereto via the image fiber 103; an excitation light cutoff filter 302 that cuts off light having a wavelength near that of the excitation light from the fluorescence image; an optical transmitting filter 303 that extracts light within a desired wavelength band from the fluorescence image transmitted by the excitation light cutoff filter 302; a filter rotating means 304 for rotating the optical transmitting filter 303; a fluorescent light focusing lens 305 for focusing the fluorescence image transmitted by the optical transmitting filter 303; a high-sensitivity fluorescent image obtaining element 306 for obtaining the fluorescent image focused by the fluorescent light focusing lens 305; and an AD converter 307 for converting the fluorescence image obtained by high-sensitivity fluorescent image obtaining element 306 to digital values to obtain image data thereof.

Figure 2:
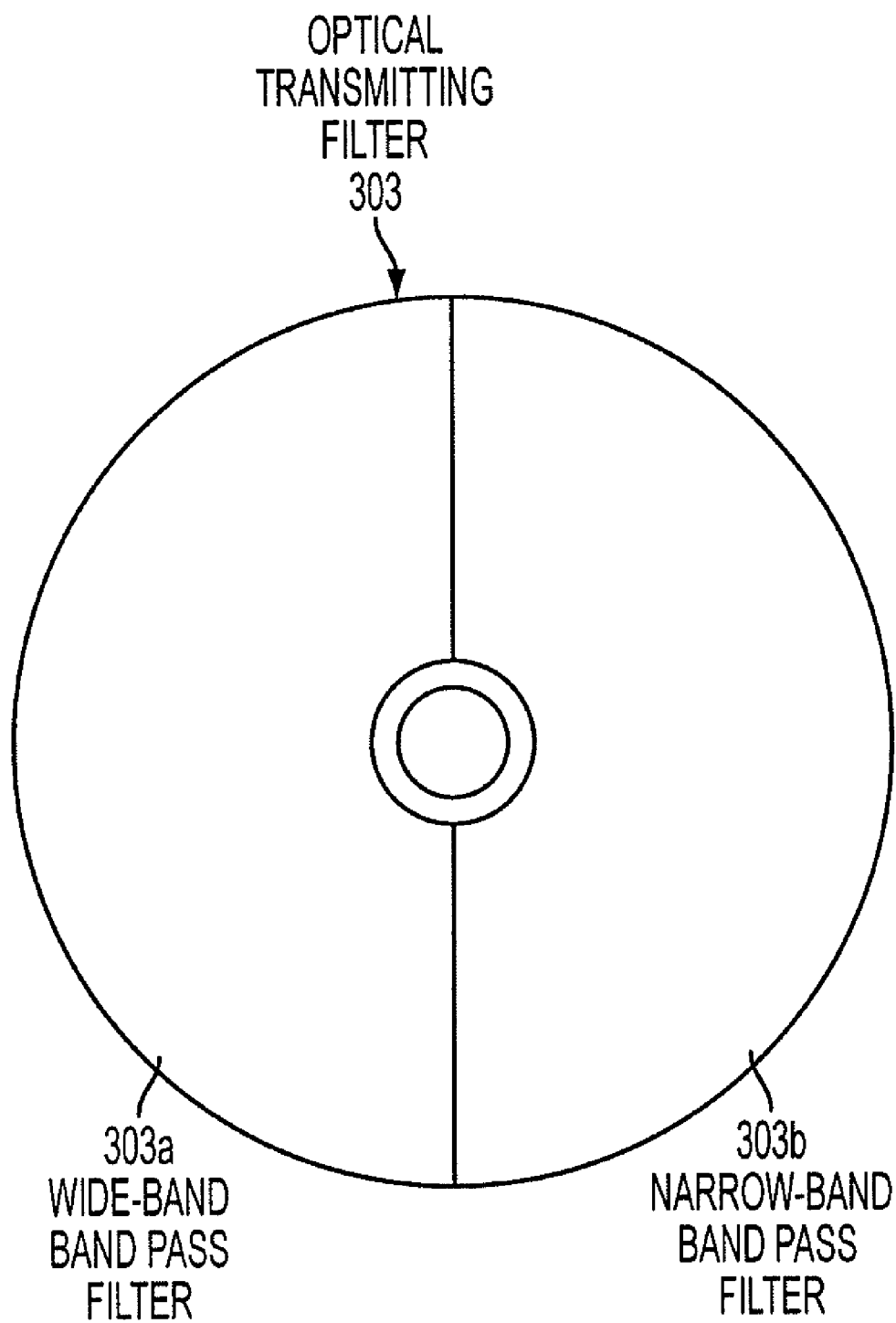
FIG. 2 is a schematic drawing of the optical transmitting filter utilized in the fluorescent endoscope according to the first embodiment (the first thereof)

As shown in FIG. 2, the optical transmitting filter 303 comprises two types of band pass filters: a band pass filter 303a and a band pass filter 303b. The band pass filter 303a is a band pass filter that transmits a fluorescence image formed of light having wavelengths within the 430-730 nm wide wavelength band; the band pass filter 303b is a band pass filter that transmits a fluorescence image formed of light having wavelengths within the 430-530 nm narrow wavelength band. Therefore, according to the image detecting unit 300: a fluorescent image data representing a wide band fluorescent image is obtained by use of a wide-band band pass filter 303a, and a fluorescent image data representing a narrow band fluorescent image is obtained by use of a narrow-band band pass filter 303b.

Figure 3:
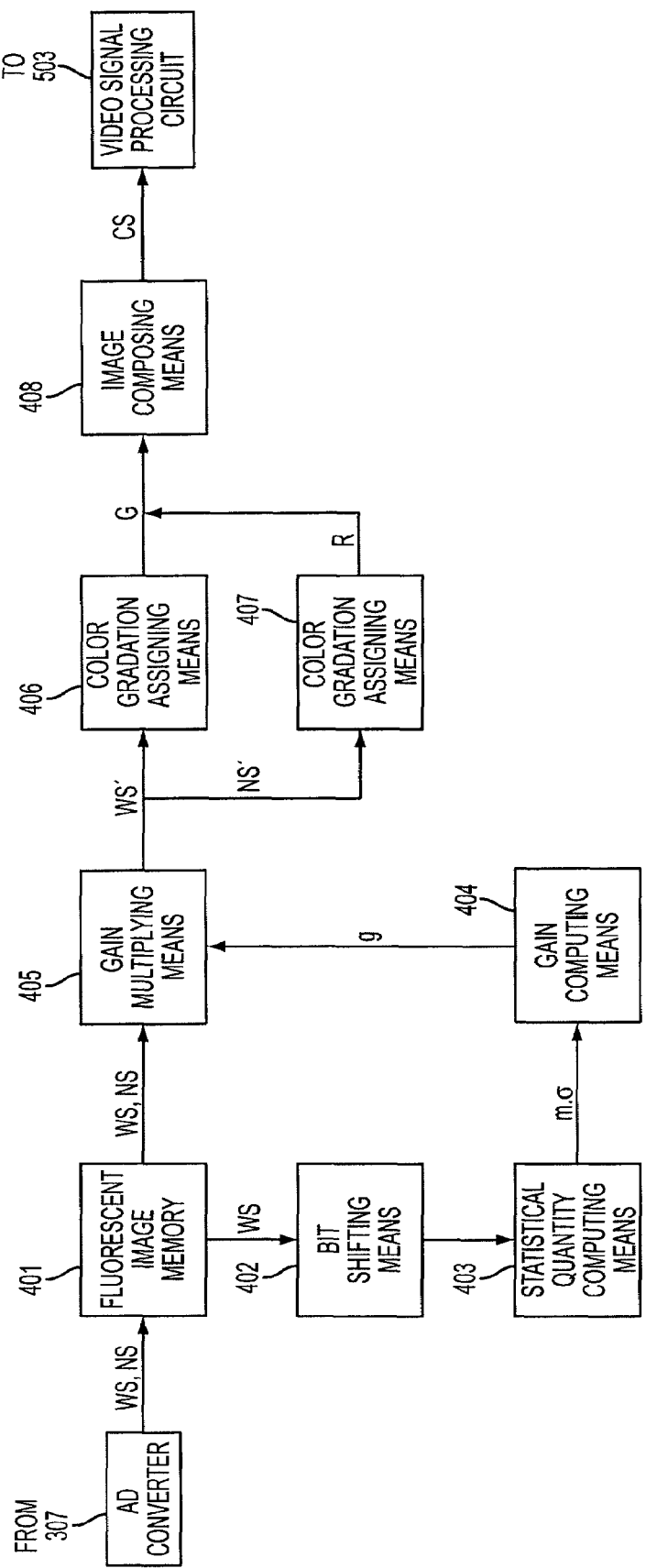
FIG. 3 is a schematic block diagram of the configuration of the image computing unit of the fluorescent endoscope according to the first embodiment of the present invention.

FIG. 3 is a schematic block diagram of the configuration of the image computing unit 400. As shown in FIG. 3, the image computing unit 400 comprises: a fluorescent image memory 401 that stores the wide band fluorescent image data WS and the narrow band fluorescent image data NS that has been obtained by the image processing unit 300; a bit shifting means 402 for shifting the data of each pixel value among the pixel values of the wide band fluorescent image represented by the wide band fluorescent image data WS stored in the fluorescent image memory 401 that is constituted by nine bits or more so that each of said data is represented by eight bits of data or less; a statistical quantity computing means 403 provided with an 8-bit statistical quantity calculator for computing the statistical quantity of the wide band fluorescent image data WS outputted from the bit shifting means 402; a gain computing means 404 for computing, based on the statistical quantity outputted from the statistical quantity computing means 403, a gain g that the wide band fluorescent image data WS and the narrow band fluorescent image data NS are to be multiplied by; a gain multiplying means 405 for multiplying the wide band fluorescent image data WS and the narrow band fluorescent image data NS by the gain g obtained by the gain computing means 404 to obtain a wide band fluorescent image data WS' and a narrow band fluorescent image data NS', which have been multiplied by the gain g; a color gradation assigning means 406 for assigning a green (G) color gradation to the wide band fluorescent image data WS' outputted from the gain multiplying means 405; a color gradation assigning means 407 for assigning a red (R) color gradation to the narrow band fluorescent image data NS' outputted from the gain multiplying means 405; and an image composing means 408 for colorizing and synthesizing the wide band fluorescent image data WS' and the narrow band fluorescent image data NS' outputted from the color gradation assigning means 406 and 407, respectively, to obtain a composite image data CS representing a composite image.

Note that according to the current embodiment, the wide band fluorescent image data WS and the narrow band fluorescent image data NS have both been stored in the fluorescent image memory 401; however, each can be stored in respective separate memories.

The display signal processing unit 500 comprises: an AD converter 501 that digitizes the visible image signal obtained by the standard image obtaining element 107 to obtain a standard image data; a standard image memory 502 that stores the standard image data; and a video signal processing circuit 503 that converts the standard image data outputted by the standard image memory 502 and the composite-image image data outputted from the image composing means 408 to video signals and outputs said video signals.

The monitor 600 is provided with a standard image monitor 601 and a composite image monitor 602.

Next, the operation of the fluorescent endoscope according to the first embodiment of the configuration described above will be explained. In order to obtain two fluorescence images, each formed of a mutually different wavelength band of fluorescent light, first, based on a signal outputted from the control computer 200, the semiconductor laser power source 112 is activated, and the GaN type semiconductor laser 111 emits excitation light Lr having a wavelength of 410 nm. The excitation light Lr emitted by the GaN type semiconductor laser 111 is transmitted by an excitation light focusing lens 113 and enters the excitation light guide 101a; after being guided to the distal end of the endoscope insertion portion 100, said excitation light Lr passes through the illuminating lens 104 and is projected onto the target subject 50.

The fluorescence image Zj formed of the fluorescent light emitted from the target subject 50 upon the irradiation thereof by the excitation light Lr is focused by the focusing lens 106, enters the distal end of the image fiber 103, and enters the excitation light cutoff filter 302 via the image fiber 103. The fluorescent image Zj that has passed through the excitation light cutoff filter 302 enters the optical transmitting filter 303. Note that the excitation light cutoff filter 302 is a long pass filter that transmits all fluorescent light having a wavelength of 420 nm or longer. Because the wavelength of the excitation light is 410 nm, the excitation light reflected from the target subject 50 is cutoff by this excitation light cutoff filter 302, and does not enter the optical transmitting filter 303.

The filter rotating means 304 is driven based on a signal from the control computer 200, and after the fluorescent image Zj has passed through the band pass filter 303a, said fluorescent image Zj is focused by the fluorescent light focusing lens 305 and obtained as a wide band fluorescent image by the high sensitivity fluorescence image obtaining element 306. Further, after the fluorescent image Zj has passed through the band pass filter 303b, said fluorescent image Zj is focused by the fluorescent light focusing lens 305 and obtained as a narrow band fluorescent image by the high sensitivity fluorescence image obtaining element 306. The visible image signal from the high sensitivity fluorescence image obtaining element 306 is inputted to the AD converter 307, and after being digitized therein, is stored as a wide band fluorescent image data WS and a narrow band fluorescent image data NS in the fluorescent image memory 401. Note that the wide band fluorescent image data WS obtained by the high sensitivity fluorescence image obtaining element 306 is stored within a wide band fluorescent image region (not shown) of the fluorescent image memory 401, and the narrow band fluorescent image data WS obtained by the high sensitivity fluorescence image obtaining element 306 is stored within a narrow band fluorescent image region (not shown).

The wide band fluorescent image data WS stored in the fluorescent image memory 401 is inputted to the statistical quantity computing means 403 after being bit shifted by the bit shifting means 402 so as to be represented by an 8-bit data. The statistical quantity computing means 403 computes the average value m and the standard deviation $\sigma$ of each pixel of the wide band fluorescent image represented by the wide band fluorescent image data WS. Then, the average value m and the standard deviation $\sigma$ are inputted to the gain computing means 404, and the gain g is computed according to the above described Formula (2). Note that the maximum and minimum values of each pixel value of the wide band fluorescent image can be obtained, and the gain g computed according to the above described formula (1). Further, the gain g can be computed based the average value m and the standard deviation $\sigma$ computed of only the pixels included within a desired region within the fluorescent image (e.g., an image region having a particularly high level of interest).

The computed gain g is inputted to the gain multiplying means 405, and the gain multiplying means 405 multiplies the wide band fluorescent image data WS and the narrow band fluorescent image data NS by the inputted gain g. Note that the gain g that the wide band fluorescent image data WS and the narrow band fluorescent image data NS are multiplied by can be the same value; however, different values having a constant relationship may also be used.

The wide band fluorescent image data WS' which has been multiplied by the gain g is inputted to the color gradation assigning means 406, and the color gradation assigning means 406 assigns a G color gradation thereto. Further, the narrow band fluorescent image data NS' which has been multiplied by the gain g is inputted to the color gradation assigning means 407, and the color gradation assigning means 407 assigns an R color gradation thereto.

Figure 4:
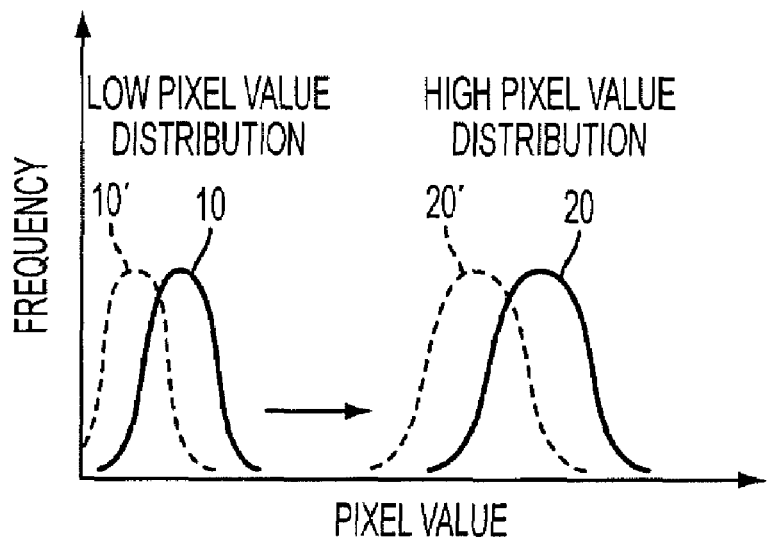
FIG. 4 is a drawing illustrating the multiplied of the gain.
Figure 5:
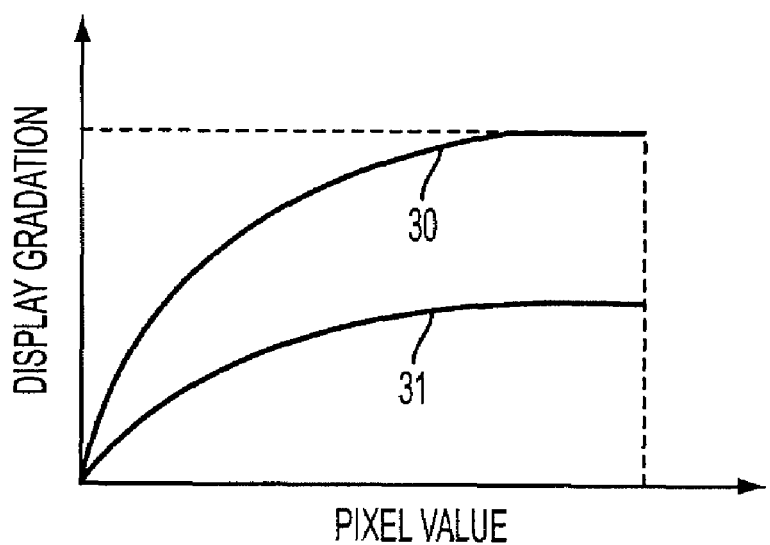
FIG. 5 is a graph showing the display gradation curves of G and R.

Here, as shown in FIG. 4, for a case in which the distribution of the pixel values of the wide band fluorescent image data WS and the narrow band fluorescent image data NS have a distribution such as that indicated by 10, 10' in the graph, by multiplying the gain g into the wide band fluorescent image data WS and the narrow band fluorescent image data NS, the distribution range of the pixel values thereof can be shifted to the high pixel value side of the graph, as indicated by 20, 20' in the graph. Then, based on the pixel value distribution range indicated by 20, 20' in the graph of FIG. 4, a G and R color gradation are assigned to the wide band fluorescent image data WS' and the narrow band fluorescent image data NS', respectively, according to the gradation process function shown in FIG. 5, for example.

The wide band fluorescent image data WS' and the narrow band fluorescent image data NS' to which G and R color gradation are assigned to, respectively, are inputted to the image composing means 408; the image composing means 408 colorizes and synthesizes the image data NS' and WS' to obtain a composite image data CS representing a composite image.

The composite image data CS is inputted to the video signal processing circuit 503, and after being DA converted therein, is inputted to the monitor unit 600 and displayed as a composite image on the composite image monitor 602. Here, normal tissue appearing in the composite image displayed on the composite image monitor 602 is shown by a bright yellow-green color, and diseased tissue appearing therein is shown by a dark green color.

Next, the operation occurring when a standard image is to be displayed will be explained. When a standard image is to be displayed, first, based on a control signal from the control computer 200, the white light source power source 115 is activated and white light Lw is emitted from the white light source 114. The white light Lw enters the white light guide 101*b* via the white light focusing lens 116, and after being guided to the distal end of the endoscope insertion portion 100, said white light Lw is emitted onto the target subject 50 from the illuminating lens 104. The light reflected from the target subject 50 upon the irradiation thereof by the white light Lw is focused by the objective lens 105, reflected by the reflective prism 108, and focused onto the standard image obtaining element 107. The visible image signal obtained by the standard image obtaining element 107 is inputted to the AD converter 501, and after being digitized therein, is stored as a standard image data in the standard image memory 502. The standard image data stored in the standard image memory 502 is inputted to the video signal processing circuit 503, and after being DA converted therein, is inputted to the monitor unit 600 and displayed as a visible image on the standard image monitor 601.

The continuous operations occurring when a composite image or a standard image is to be obtained are controlled by the control computer 200.

According to the above described endoscope implementing the fluorescence image obtaining apparatus according to the first embodiment of the present invention: a statistical quantity computing means 403 for computing the statistical quantity of the distribution of the pixel values of a wide band fluorescent image represented by a wide band fluorescence image data WS is provided; because the gain g is computed based on said statistical quantity and the wide band fluorescence image data WS and the narrow band fluorescence image data NS are multiplied by said gain, regardless of the intensity of the fluorescent light emitted from the target subject 50, a composite image data CS formed from a wide band fluorescence image data WS and a narrow band fluorescence image data NS having a desired pixel value can be obtained, and the composite image can be made to have a desired luminosity. That is to say, the luminosity of the fluorescence image, which is an effect of the intensity of the fluorescent light, can be adjusted so as to be within a desired range, whereby the distinguishability of the tissue state of the target subject can be improved.

Further, because the statistical quantity has been taken as a combination of the average value m and the standard deviation σ of the distribution of the pixel values of the wide band fluorescence image data WS, the computation of the statistical quantity can be performed comparatively easily, and an appropriate display gradation can be assigned.

Still further, for cases in which the statistical quantity computing means 403 is a means for computing the statistical quantity from a desired region of a reflectance image, the amount of computation required can be reduced.

In addition, because a bit shifting means 402 has been provided for shifting the data of the pixel values of the wide band fluorescence image data WS for cases in which said pixel values are represented by nine or more bits of data, so that said data is constituted of eight bits of data, and the statistical quantity computing means 403 is a means for computing the statistical quantity based on the bit shifted data, a common 8-bit calculator can be used as the statistical quantity computing means 403, and the speed with which the computational processes are performed can be increased.

Figure 6:
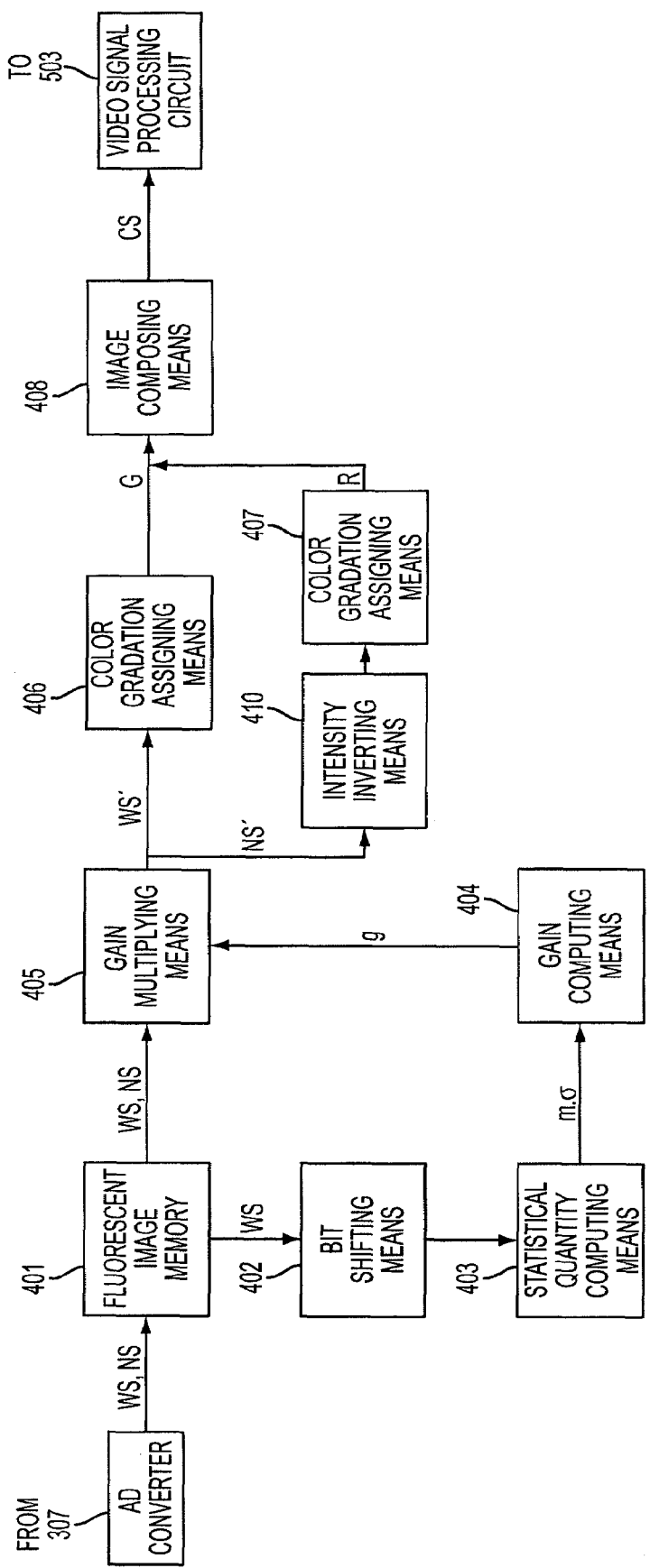
FIG. 6 is a schematic block diagram of the configuration of the image computing unit of the fluorescent endoscope according to the second embodiment of the present invention.

Next, an endoscope implementing the fluorescence image obtaining apparatus according to the second embodiment of the present invention will be explained. According to the endoscope implementing the fluorescence image obtaining apparatus according to the second embodiment: the image computing unit 400 of the first embodiment inverts the intensity of the narrow band fluorescent image data NS', which has been multiplied by the gain g, to obtain a reverse narrow band fluorescent image data NS''; and assigns a R color gradation is to the reverse narrow band fluorescent image data NS''. Therefore, as shown in FIG. 6, the image computing unit 400 of the endoscope according to the second embodiment is provided with an intensity inverting means 410 for inverting the intensity of the narrow band fluorescent image data NS', which has been multiplied by the gain g.

The intensity inverting means 410 subtracts, for cases in which the narrow band fluorescent image data NS' is represented by 8-bit data, each pixel value of the fluorescent image represented by the narrow band fluorescent image data NS' from 255 to obtain a subtraction value; this subtraction value is taken as the pixel value of the pixels of the fluorescent image of which the intensity has been inverted. Note that instead of subtracting from 255, the reciprocal of the pixel values (i.e., the 1/pixel value) can be taken as the pixel values of the fluorescent image of which the intensity has been inverted.

Hereinafter the operation of the second embodiment will be explained. Note that because the processes up until the multiplication of the fluorescent image data by the gain g are the same as those of the first embodiment, further explanation thereof has been omitted. According to the second embodiment: the gain g is computed based on the wide band fluorescence image data WS; the narrow band fluorescent image data NS is multiplied by the gain g to obtain a narrow band fluorescent image data NS'; the narrow band fluorescent image data NS' is inputted to the intensity inverting mean 410; the intensity inverting means 410 inverts the intensity of the narrow band fluorescent image data NS' to obtain a reverse narrow band fluorescent image data NS", assigns an R color gradation to the reverse narrow band fluorescent image data NS", and then combines the reverse narrow band fluorescent image data NS" and the wide band fluorescence image data WS', to which a green color gradation has been assigned, to obtain a composite image data CS.

Figure 7A:
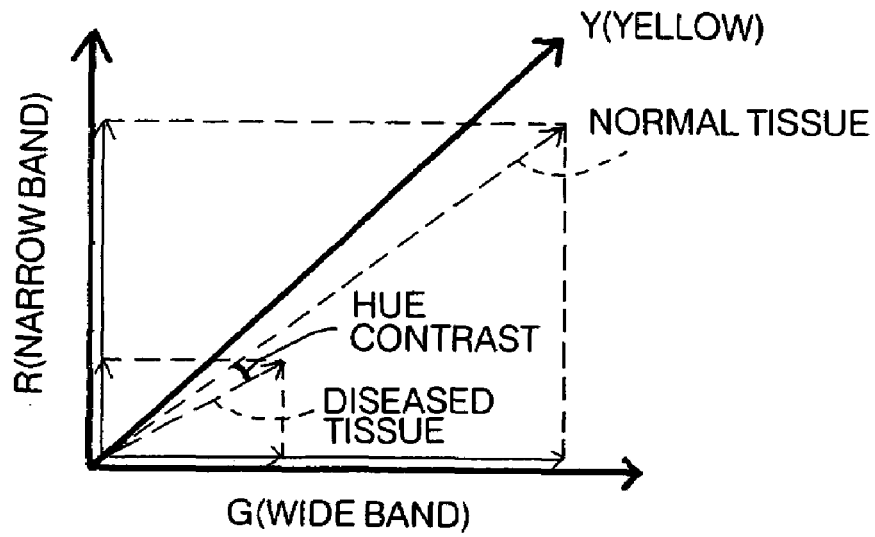
FIGS. 7A and 7B are graphs illustrating the intensity inversion.

Here, the effect of the inversion of the intensity will be explained. FIG. 7 is a graph illustrating the effect of the intensity inversion. As shown in FIG. 7A, if a two-dimensional colorized space having a horizontal axis G and a vertical axis R is considered, before the inversion of the intensity is performed, because the ratio of the wide band fluorescence image data WS' and the narrow band fluorescence image data NS' of the normal tissue is such that the wide band fluorescence image data WS' side is slightly larger, the normal tissue is shown as a bright yellow-green color in the composite image. On the other hand, the intensity of the diseased portion is reduced, and in comparison to the normal tissue, because the ratio of the wide band fluorescence image data WS' and the narrow band fluorescence image data NS' of the normal tissue is such that value of the wide band fluorescence image data WS' is larger, opposed to that of the narrow band fluorescence image data NS'; accordingly, the diseased tissue is shown as a dark green color in the composite image. In this manner, although the normal tissue and the diseased tissue are shown as a greenish yellow color and a dark green color, respectively, in the composite image, because the difference in the hue contrast is slight, there are cases in which it is difficult to distinguish between the normal tissue and the diseased tissue.

Figure 7B:
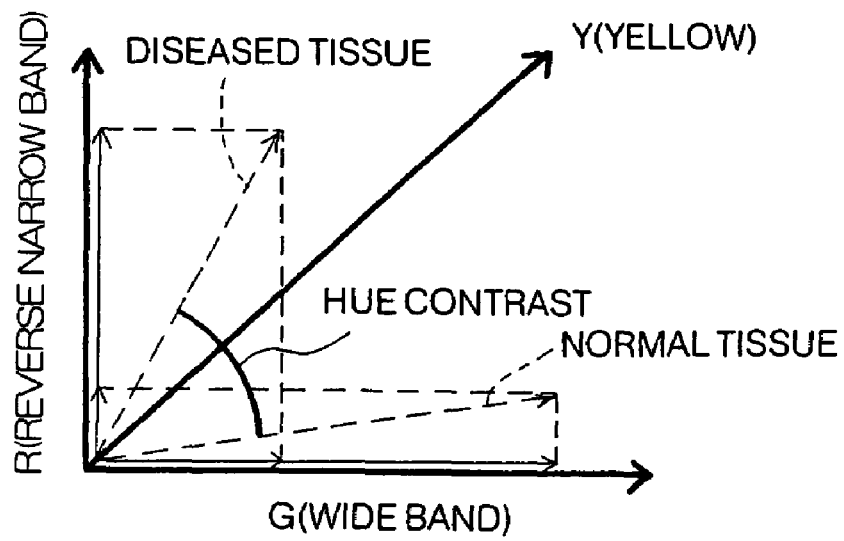

In contrast to this, as shown in FIG. 7B, if the intensity of the narrow band fluorescent image data NS' is inverted, because the change occurring in the intensity of the fluorescent light emitted from the diseased tissue occurs as an reverse phase change in the wide band fluorescence image data WS' and the narrow band fluorescence image data NS', the value of the narrow band fluorescent image data NS' becomes larger than that of the wide band fluorescence image data WS'. Therefore, the normal tissue is shown as a bright green color and the diseased tissue as a bright red color, and the difference between the hue contrast of the normal tissue and the diseased tissue becomes enlarged in comparison to the state prior to the inversion of the intensity of the narrow band fluorescent image data NS'. Therefore, according to the second embodiment described above, by inverting the intensity of the narrow band fluorescent image data NS', the difference between the normal tissue and the diseased tissue appearing in the composite image can be rendered more clearly, whereby the distinguishability of the tissue state of the target subject can be improved a level.

Figure 8:
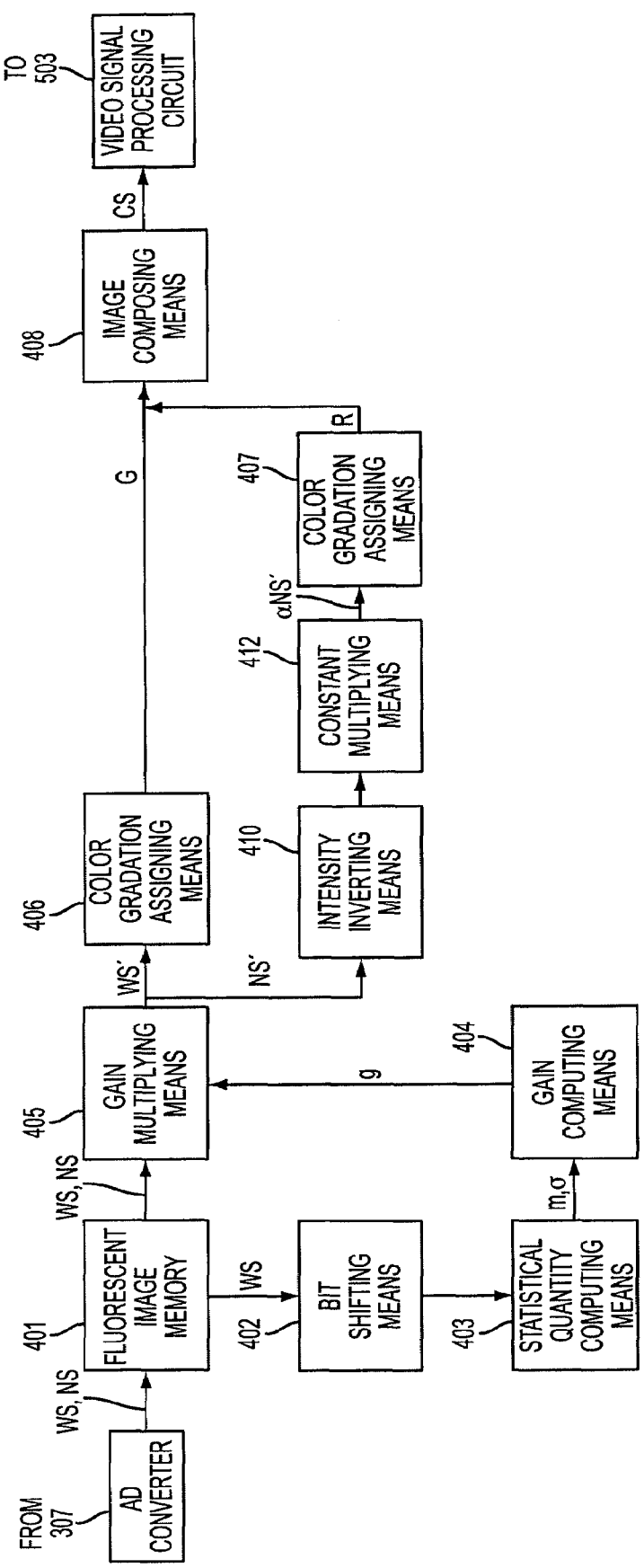
FIG. 8 is a schematic block diagram of the configuration of the image computing unit of the fluorescent endoscope according to the third embodiment of the present invention.

Next, an endoscope implementing the fluorescence image obtaining apparatus according to the third embodiment of the present invention will be explained. According to the endoscope implementing the fluorescence image obtaining apparatus according to the third embodiment: the image computing unit 400 of the second embodiment inverts the intensity of the narrow band fluorescent image data NS', which has been multiplied by the gain g, to obtain a reverse narrow band fluorescent image data NS"; then, multiplies the reverse narrow band fluorescent image data NS" by a predetermined constant $\alpha$ ($\alpha>1$) to obtain a constant-multiplied reverse narrow band fluorescence image NS"; and assigns a R color gradation to the constant-multiplied reverse narrow band fluorescent image data NS", which has been multiplied by the constant $\alpha$. Therefore, as shown in FIG. 8, the image computing unit 400 of the endoscope according to the third embodiment comprises: an intensity inverting means 410 for inverting the intensity of the narrow band fluorescent image data NS', which has been multiplied by the gain g, to obtain a reverse narrow band fluorescent image data NS"; and a constant multiplying means 412 for multiplying the reverse narrow band fluorescent image data NS" by a predetermined constant $\alpha$ to obtain a constant-multiplied reverse narrow band fluorescent image data NS".

Hereinafter the operation of the third embodiment will be explained. Note that because the processes up until the multiplication the fluorescent image data by the gain g are the same as those of the first embodiment, further explanation thereof has been omitted. According to the third embodiment: the gain g is computed based on the wide band fluorescence image data WS; the narrow band fluorescent image data NS is multiplied by the gain g to obtain a narrow band fluorescent image data NS'; the narrow band fluorescent image data NS' is inputted to the intensity inverting mean 410; and the intensity inverting means 410 inverts the intensity of the narrow band fluorescent image data NS' to obtain a reverse narrow band fluorescent image data NS". Then, the reverse narrow band fluorescent image data NS" is inputted to the constant multiplying means 412, and the constant multiplying means 412 multiplies the reverse narrow band fluorescent image data NS" by a predetermined constant $\alpha$ to obtain a constant-multiplied reverse narrow band fluorescent image data NS". An R color gradation is assigned to the narrow band fluorescence image data NS", which has been multiplied by the constant $\alpha$, a G color gradation is assigned to the wide band fluorescence image data WS', then the two are combined to form a composite image data CS.

In the case that the narrow band fluorescence data NS' is intensity inverted, the dark portions included in the composite image other than diseased tissue also become red in color, thereby making ambiguous the difference between diseased tissue and these dark portions. Therefore, according to the third embodiment, the constant multiplying means 412 multiplies a constant $\alpha$ to the narrow band fluorescence data NS', which has been intensity inverted, whereby the effect causing the dark portions occurring in the composite image to also become red in color can be suppressed, preventing the misrecognition of the diseased tissue and the portions that are simply dark, and thereby improving the distinguishability of the tissue state by a level.

Note that according to the second and third embodiments, although the intensity of the narrow band fluorescent image data NS' has been inverted, the intensity of the wide band fluorescence image data WS may be inverted instead.

Figure 9:
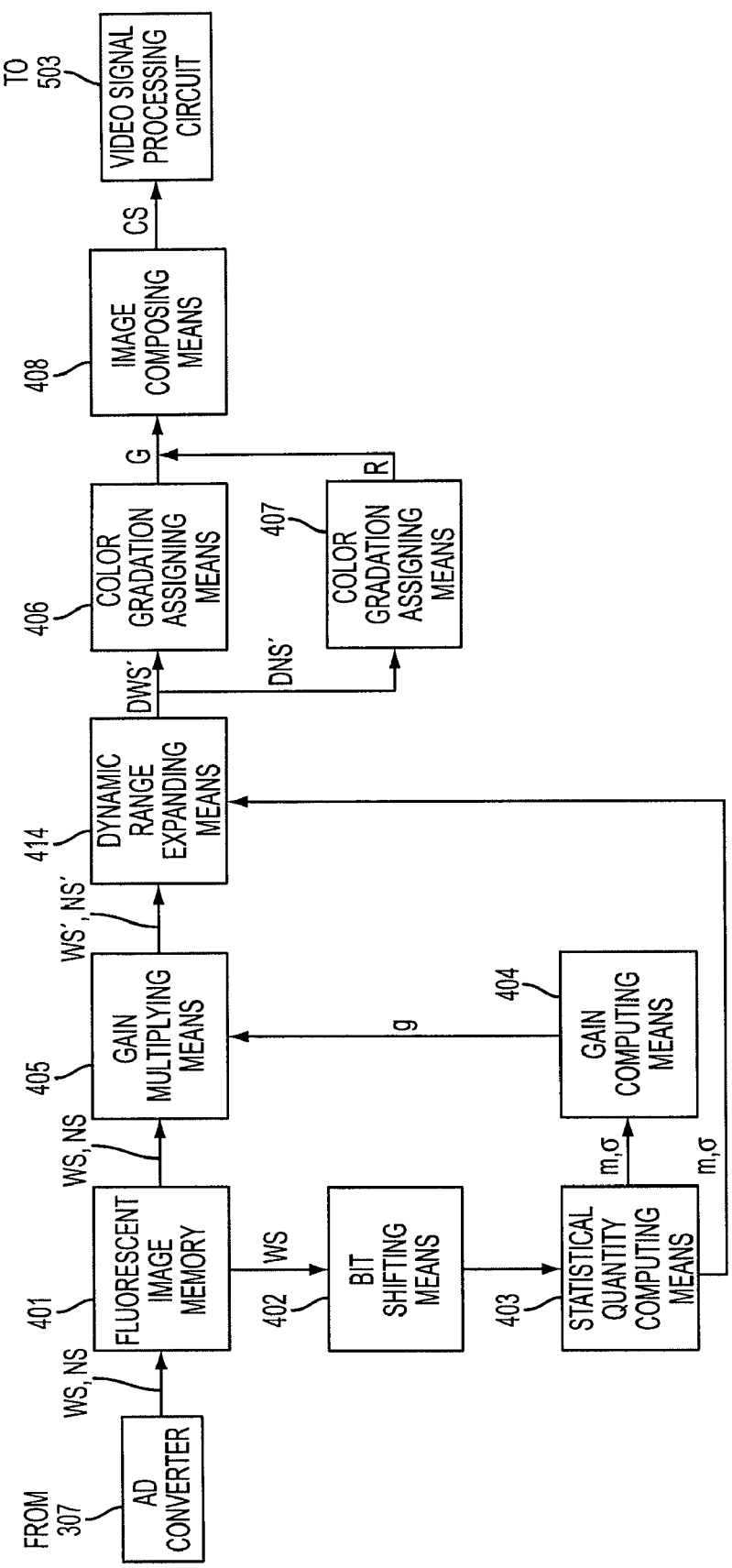
FIG. 9 is a schematic block diagram of the configuration of the image computing unit of the fluorescent endoscope according to the fourth embodiment of the present invention.

Next, an endoscope implementing the fluorescence image obtaining apparatus according to the fourth embodiment of the present invention will be explained. According to the endoscope implementing the fluorescence image obtaining apparatus according to the fourth embodiment: the image computing unit 400 of the first embodiment subjects the narrow band fluorescent image data NS' and the wide band fluorescent image data WS', which have been multiplied by the gain g, to a dynamic range expansion process, based on the statistical quantity computed by the statistical quantity computing means 403. Therefore, as shown in FIG. 9, the image computing unit 400 of the endoscope according to the fourth embodiment is provided with a dynamic range expanding means 414 for subjecting the narrow band fluorescent image data NS' and the wide band fluorescent image data WS' to a dynamic range expansion process.

As shown in the Formula (3) below, the dynamic range expanding means 414 computes, based on the average value m and the standard deviation σ of each pixel of the wide band fluorescent image computed by the statistical quantity computing means 403, the distribution range of the pixel values of each fluorescence image represented by the wide band fluorescence image data DWS' and the narrow band fluorescent image data DNS', which have been subjected to the dynamic range expansion process. Note that in the Formula (3), b=2, for example.

$$\text{Distribution range} = m - b \times \sigma \text{ to } m + b \times \sigma \tag{3}$$

Then, if the minimum value (Min) is designated as m−b×σ, the maximum value (Max) as m+b×σ, each pixel value of each fluorescent image that has been subjected to the dynamic range expansion process can be computed by use of the function g (x) (where x equals the pixel values of the narrow band fluorescent image and the wide band fluorescent image which have been multiplied by the gain g) shown in the Formula (4) below.

$$g(x) = (x - \text{Min})/(\text{Max} - \text{Min}) \tag{4}$$

Hereinafter the operation of the fourth embodiment will be explained. Note that because the processes up until the multiplication of the gain g into the fluorescent image data are the same as those of the first embodiment, further explanation thereof has been omitted. According to the fourth embodiment: the gain g is computed based on the wide band fluorescence image data WS; the narrow band fluorescent image data NS and the wide band fluorescent image data WS are multiplied by the gain g to obtain a narrow band fluorescent image data NS' and a wide band fluorescent image data WS', which have been multiplied by the gain g; the narrow band fluorescent image data NS' and the wide band fluorescence image data WS' are inputted to the dynamic range expanding means 414, and are subjected to the dynamic range expansion process therein to obtain a the wide band fluorescence image data DWS' and a narrow band fluorescent image data DNS'. The wide band fluorescence image data DWS' and the narrow band fluorescent image data DNS' are assigned an R color gradation and a G color gradation, respectively, and are then combined to obtain a composite image data CS.

Figure 10A:
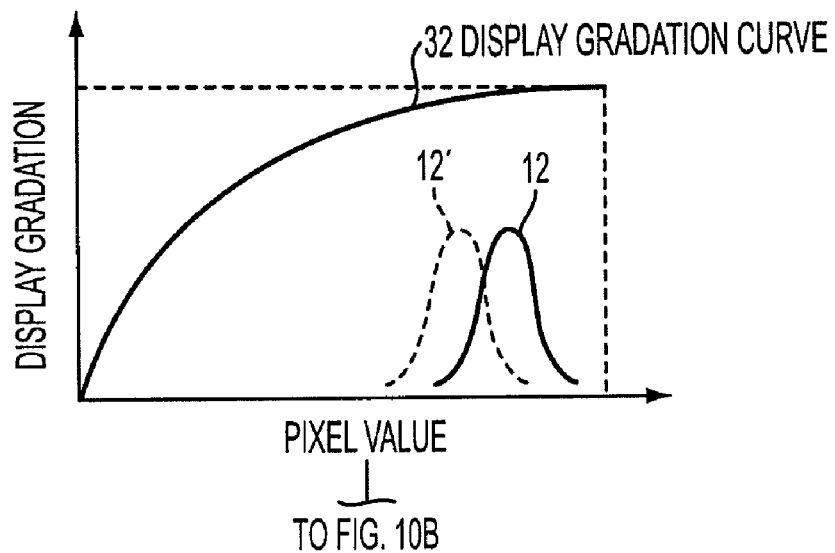
FIGS. 10A and 10B are graphs illustrating the dynamic range expansion process.
Figure 10B:
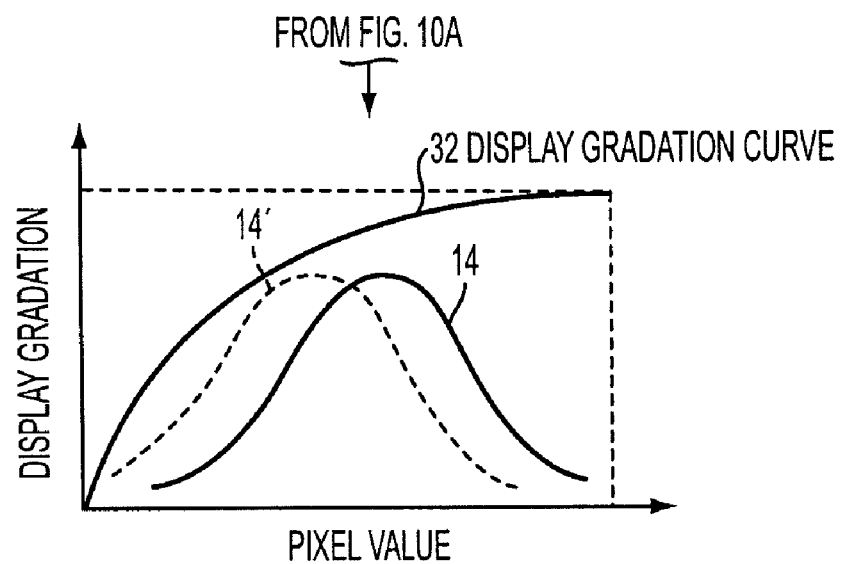

Here, as shown in FIG 10A, for cases in which the distribution of the pixel values of the wide band fluorescence image and the narrow band fluorescent image prior to the subjection thereof to the dynamic range expansion process is that indicated by 12, 12' in the graph, because the distribution range thereof is present on only a portion of the display gradation curve 32 of the composite image monitor 602, the contrast of the composite image formed thereof would not be very high. In contrast to this, by subjecting the wide band fluorescence image and the narrow band fluorescent image to the dynamic range expansion process, the distribution range of the pixel values thereof can be made to span substantially the entire area of the display gradation curve 32 of the composite image monitor 602, as indicated by 14, 14' in the graph shown in FIG. 14B, whereby the contrast of the composite image formed thereof can be made higher. Accordingly, the change in the tissue state of the target subject 50 can be represented more accurately in the composite image, whereby the distinguishability of the tissue state of the target subject 50 can be further improved.

Note that for cases in which the statistical quantity computing means 403 computes the Max and Min values of each pixel of the wide band fluorescence image, the dynamic range expanding means 414 can compute the distribution range of the pixel values of each fluorescent image represented by the wide band fluorescence image data DWS' and the narrow band fluorescent image data DNS', which have been subjected to the dynamic range expansion process, by use of the Formula (5) below. Note that in Formula (5), c and d are arbitrary constants.

$$\text{Distribution range} = (\text{Max} + \text{Min})/2 - c \times (\text{Max} - \text{Min})/2 \text{ to } (\text{Max} + \text{Min})/2 + d \times (\text{Max} - \text{Min})/2 \tag{5}$$

Further, according to the fourth embodiment, when the normal tissue and the diseased tissue are adequately interspersed there is no problem; however, for cases in which only normal tissue or only diseased tissue appears in the composite image, if said composite image is subjected to the dynamic range expansion process, because the change within the tissue state of the normal tissue or within the tissue state of the diseased tissue becomes assigned to the dynamic range of the composite image monitor 602, it becomes impossible to discern whether the displayed composite image is a normal tissue or a diseased tissue.

Figure 11:
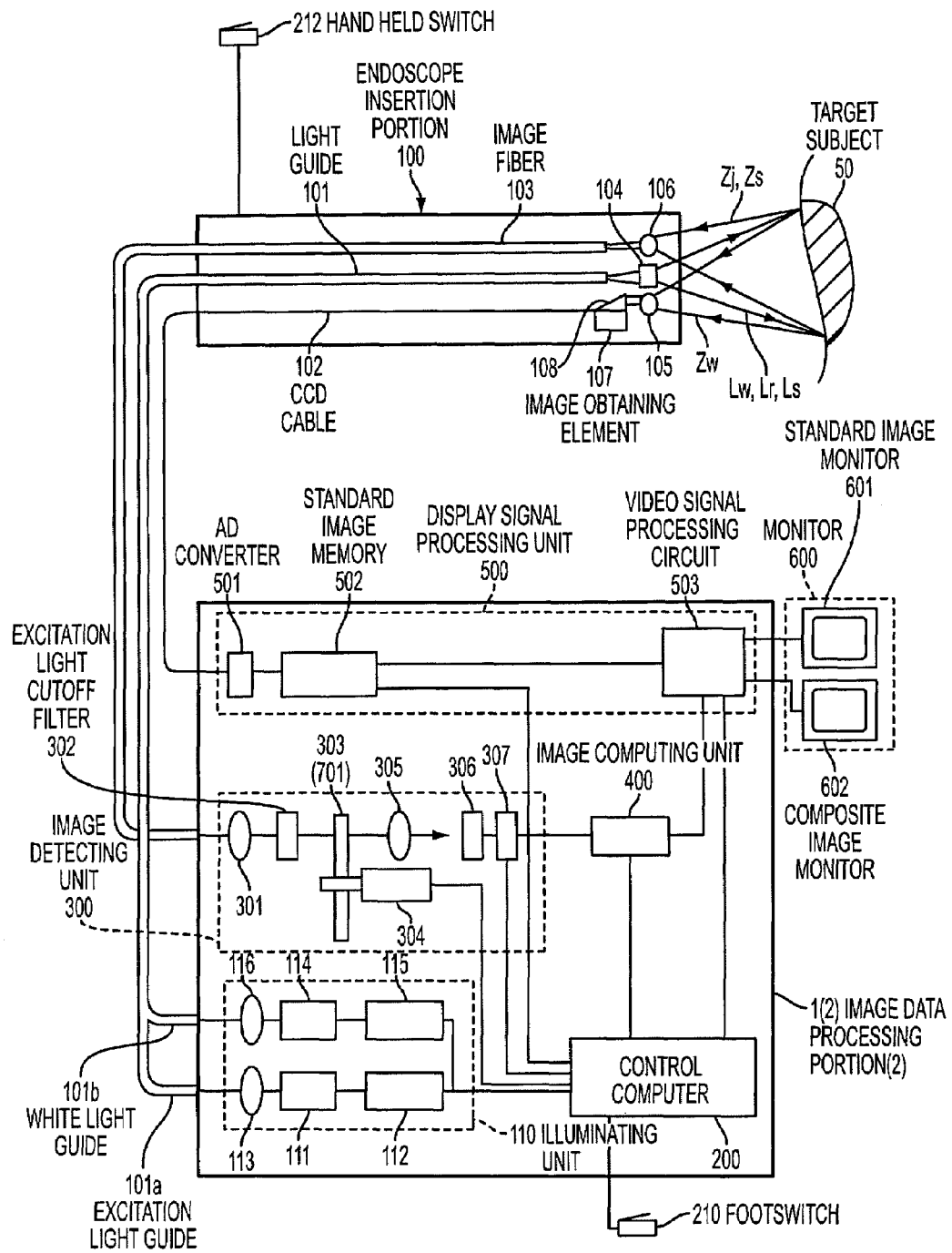
FIG. 11 is a drawing of the state in which the fluorescent endoscope according to the fourth embodiment has been provided with a foot switch or a hand operated switch.

Accordingly, the performance of the dynamic range expansion process can also be performed only at those times desired by the operator of the endoscope. In this case, the dynamic range expansion means 414 can be switched on and off by a footswitch 210 or a hand held switch 212 as shown in FIG. 11.

Further, according to the fourth embodiment described above, the dynamic range expanding means 414 has been provided on the first embodiment to perform the dynamic range process; however, it is also possible to perform the same dynamic range expansion process in the second and third embodiments. In this case, according to the second embodiment, the dynamic range expansion process can be performed on the reverse narrow band fluorescent image data NS", which has been obtained by the reversal of the intensity of the narrow band fluorescent image data NS' by the intensity inverting means 410; in the third embodiment, the dynamic range expansion process can be performed on the constant-multiplied reverse narrow band fluorescent image data NS".

Note that according to the first through the fourth embodiments described above, a G color gradation has been assigned to the wide band fluorescence image data WS' (included those of which the dynamic range has been expanded) and an R color gradation has been assigned to the narrow band fluorescent image data NS' (including those of which the dynamic range has been expanded, those of which the intensity thereof has been inverted, and those that have been multiplied by the constant α); however, an R color gradation can be assigned to the wide band fluorescence image data WS', and a G color gradation can be assigned to the narrow band fluorescent image data NS'. Further, in addition to the G and R color gradations, a B color gradation may be assigned as well. In this case, a G and a B color gradation can be assigned to the wide band fluorescence image data WS', and an R color gradation can be assigned to the narrow band fluorescent image data NS'; alternatively, a G and a B color gradation can be assigned to the narrow band fluorescence image data NS', and an R color gradation can be assigned to the wide band fluorescent image data WS'. Note that the change in the assignment of the color gradations may be performed after the fluorescent images have been subjected to the dynamic range expansion process, the constant α multiplying process, or the intensity inversion process.

Figure 12:
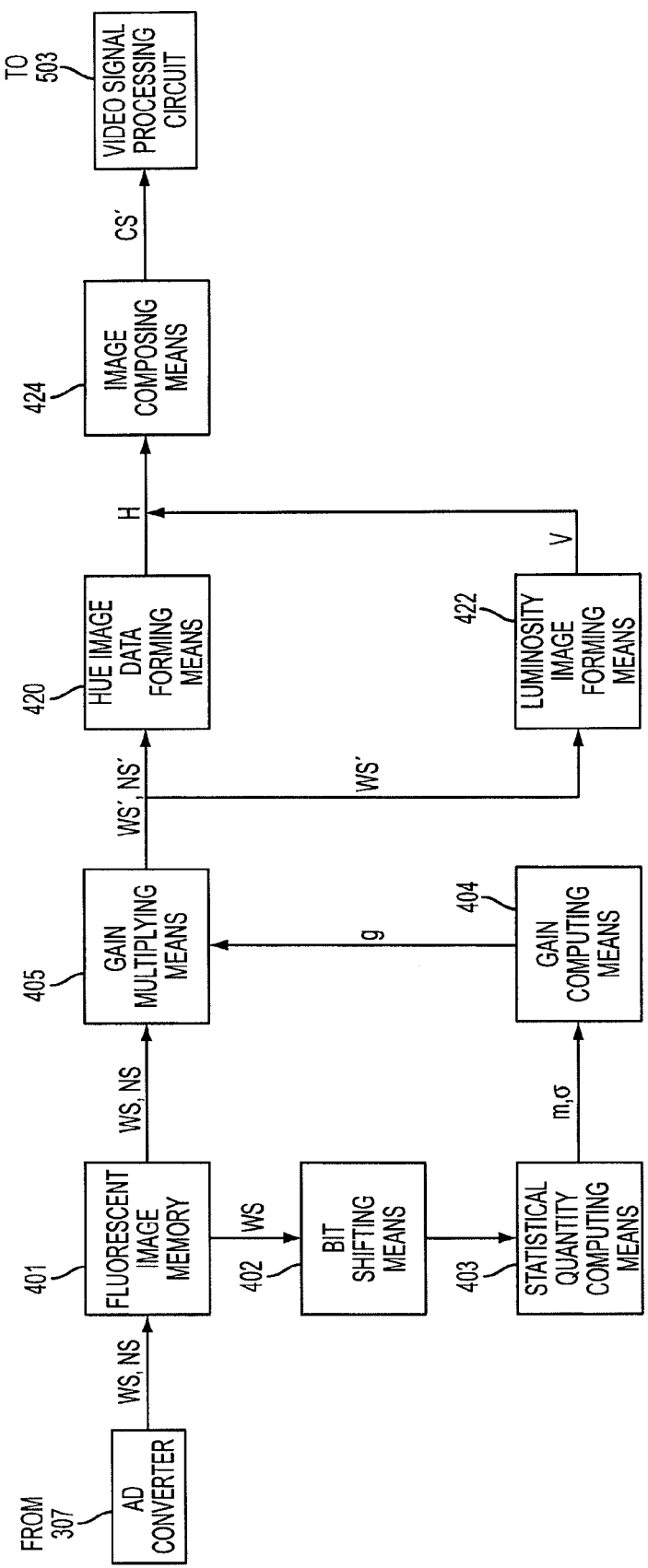
FIG. 12 is a schematic block diagram of the configuration of the image computing unit of the fluorescent endoscope according to the fifth embodiment of the present invention.

Next, an endoscope implementing the fluorescence image obtaining apparatus according to the fifth embodiment of the present invention will be explained. According to the endoscope implementing the fluorescence image obtaining apparatus according to the fifth embodiment: as in the first embodiment, a hue image data is obtained of the narrow band fluorescent image data NS' and the wide band fluorescent image data WS', which has been multiplied by the gain g, and a luminosity image data is obtained of the wide band fluorescent image data WS', and the hue image data and the luminosity image data are combined to obtain a composite image data. Therefore, as shown in FIG. 12, the image computing unit 400 of the endoscope according to the fifth embodiment comprises: a hue image data forming means 420, instead of the hue gradation assigning means 406, the hue gradation assigning means 407 and the image composing means 408, for forming a hue data H, which represents a hue, from the narrow band fluorescent image data NS' and the wide band fluorescent image data WS', which has been multiplied by the gain g; a luminosity image data forming means 422 for forming, based on the wide band fluorescent image data WS', a luminosity image data V representing a brightness; and an image composing means 424 for combining the hue data H and the luminosity image data V to obtain a composite image data CS'.

The hue image data forming means 420 outputs the wide band fluorescent image data WS' and the narrow band fluorescent image data NS', which has been multiplied by the gain g, to respectively different color planes (e.g., G, R), and forms, based on the additive color mixture method, a color added and mixed image data representing a color added and mixed image; then, by computing, based on this color added and mixed image data, the hue value, of the color added and mixed image represented by said color added and mixed image data, occurring in the Munsell color system, the hue image data forming means 420 forms a hue data value H.

The luminosity image data forming means 422 refers to a prerecorded look-up table correlating the range of the pixel values of the wide band fluorescent image which has been multiplied by the gain g represented by the wide band fluorescent image data WS' and a luminosity V (Value) occurring in the Munsell color system, and forms a luminosity image data V.

Hereinafter the operation of the fifth embodiment will be explained. Note that because the processes up until the multiplication of the fluorescent image data by the gain g are the same as those of the first embodiment, further explanation thereof has been omitted. According to the fifth embodiment: the narrow band fluorescent image data NS' and the wide band fluorescence image data WS', which has been multiplied by the gain g, are inputted to the hue image data forming means 420. Next, the hue image data forming means 420 outputs the wide band fluorescent image data WS' and the narrow band fluorescent image data NS' to respectively different color planes, and forms, based on the additive color mixture method, a color added and mixed image data representing a color added and mixed image; then, by computing, based on this color added and mixed image data, the hue value of the color added and mixed image represented by said color added and mixed image data and occurring in the Munsell color system, the hue image data forming means 420 forms a hue data value H.

Meanwhile, the wide band fluorescent image data WS', which has been multiplied by the gain g, is inputted to the luminosity image data forming means 422; then, the luminosity image data forming means forms, based on the range of the pixel values of the wide band fluorescent image represented by the wide band fluorescent image data WS' and the look-up table, a luminosity image data V determining a luminosity V (Value) occurring in the Munsell color system.

The hue image data H and the luminosity image data V are inputted to the image composing means 424, and the image composing means 424 forms a composite image data CS'. In this case, because a saturation is required in addition to the hue and luminosity, when the composite image CS' is to be composed, the largest value of each hue and each luminosity is set as a saturation value S occurring in the Munsell color system, and the composite image CS' is formed by performing an RGB conversion process. The formed composite image CS' is displayed on the composite image monitor 602. Note that the setting of the saturation may alternatively be set according to the preferences of the operator.

Here, according to the above-described fifth embodiment, by combining a hue image data H is formed from the wide band fluorescent image and the narrow band fluorescent image with a luminosity image data V to form a composite image CS', the hue of the composite image CS' displayed on the composite image monitor 602 becomes a hue that reflects the tissue state of the target subject 50, and the luminosity reflects the form of the target subject 50. Accordingly, data relating to the tissue state of the target subject 50 as well as data relating to the form of the target subject 50 can be displayed concurrently in a single image.

Figure 13:
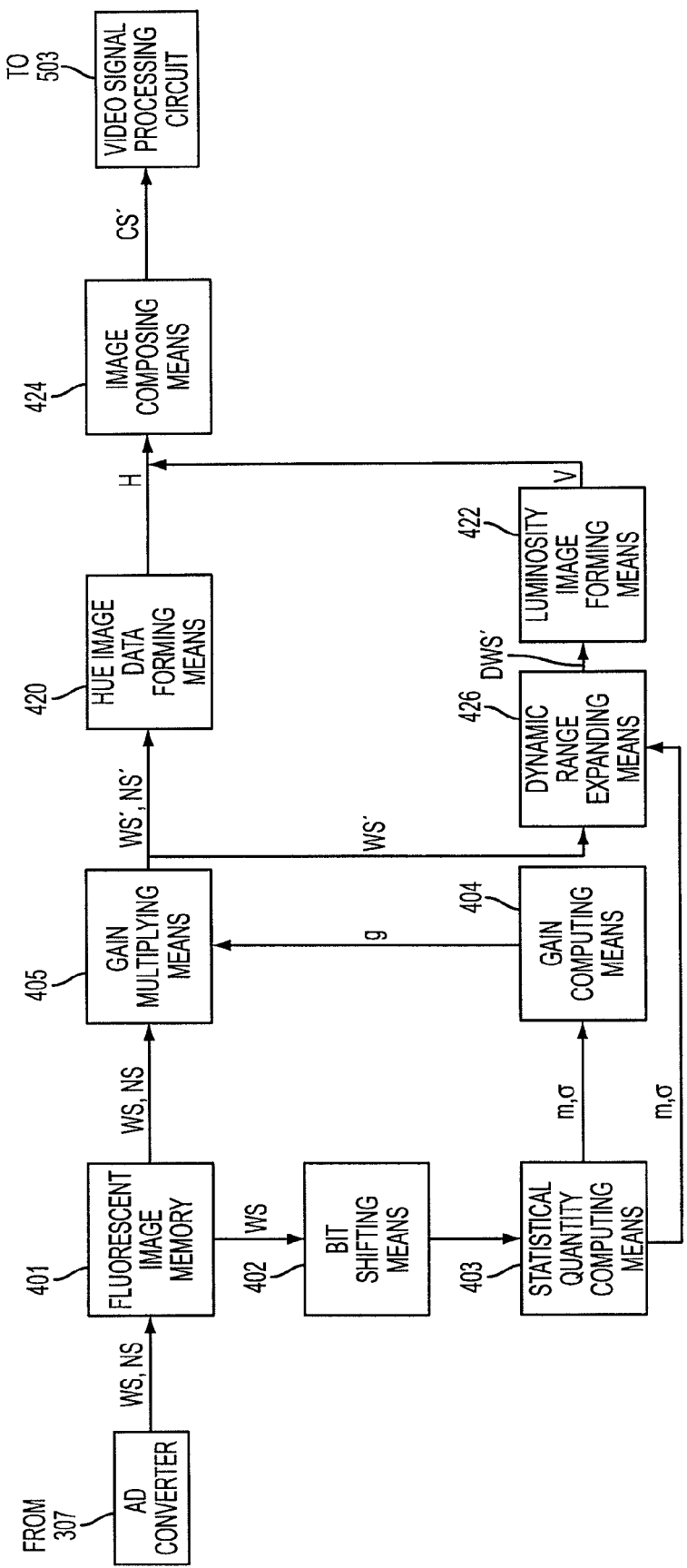
FIG. 13 is a schematic block diagram of the configuration of the image computing unit of the fluorescent endoscope according to the sixth embodiment of the present invention.

Next, an endoscope implementing the fluorescence image obtaining apparatus according to the sixth embodiment of the present invention will be explained. According to the endoscope implementing the fluorescence image obtaining apparatus according to the sixth embodiment: the narrow band fluorescent image data NS' and the wide band fluorescent image data WS', which have been multiplied by the gain g, as in the fifth embodiment, are subjected to a dynamic range expansion process, based on the statistical quantity computed by the statistical quantity computing means 403. Therefore, as shown in FIG. 13, the image computing unit 400 of the endoscope according to the sixth embodiment is provided with a dynamic range expanding means 426 for subjecting the wide band fluorescent image data WS', which has been multiplied by the gain g, to a dynamic range expansion process. Note that because the dynamic range expanding means 426 performs the same process as that performed by the dynamic range expanding means 414 of the fourth embodiment, a detailed explanation thereof has been omitted.

In this manner, by providing the dynamic range expanding means 426, because the distribution of the luminosity image data V can be made to span substantially the entire area of the display gradation curve of the composite image monitor 602, the contrast of the composite image formed thereof can be made higher. Accordingly, the change in the tissue state of the target subject 50 can be represented more accurately in the composite image, whereby the distinguishability of the tissue state of the target subject 50 can be further improved.

Note that according to the sixth embodiment, the dynamic expansion process can be preset so as to be performed for each image, or can be performed only when so desired by the operator of the endoscope, by use of a foot switch 210 or a hand operated switch 212, in the same manner as in the fourth embodiment.

Further, according to the above-described fifth and sixth embodiments, although hue image data H and luminosity image data V have been formed in addition to the processes performed in the first embodiment, it is also possible that a hue image data H and luminosity image data V be formed and combined to obtain a composite image data CS' in the second through fourth embodiments described above. In this case, according to the second embodiment, the hue image data H can be formed utilizing the reverse narrow band fluorescence image NS"; according to the third embodiment, the hue image data H can be formed utilizing the constant-multiplied reverse narrow band fluorescence image NS'". Further, according to the fourth embodiment, the hue image data H can be formed utilizing the wide band fluorescence image DWS' and the narrow band fluorescence image DNS', which have been subjected to the dynamic range expansion process.

Still further, according to the above-described fifth and sixth embodiments, although the luminosity image data V has been formed, based on the wide band fluorescent image data WS', which has been multiplied by the gain g, by the luminosity image data forming means 422, the luminosity image data V may also be formed based on the narrow band fluorescent image data NS', which has been multiplied by the gain g.

Note that according to the fifth and sixth embodiments, although the hue image H (a uniform saturation) has been computed, these embodiments are not limited thereto: an image corresponding to the the X,Y components of an XYZ color space; the ab components of a Lab color space; the uv components of a Luv color space; the a*b* components of a uniform La*b* color space; the u*v* components of a uniform Lu*v* color space; etc. can also be computed.

Figure 14:
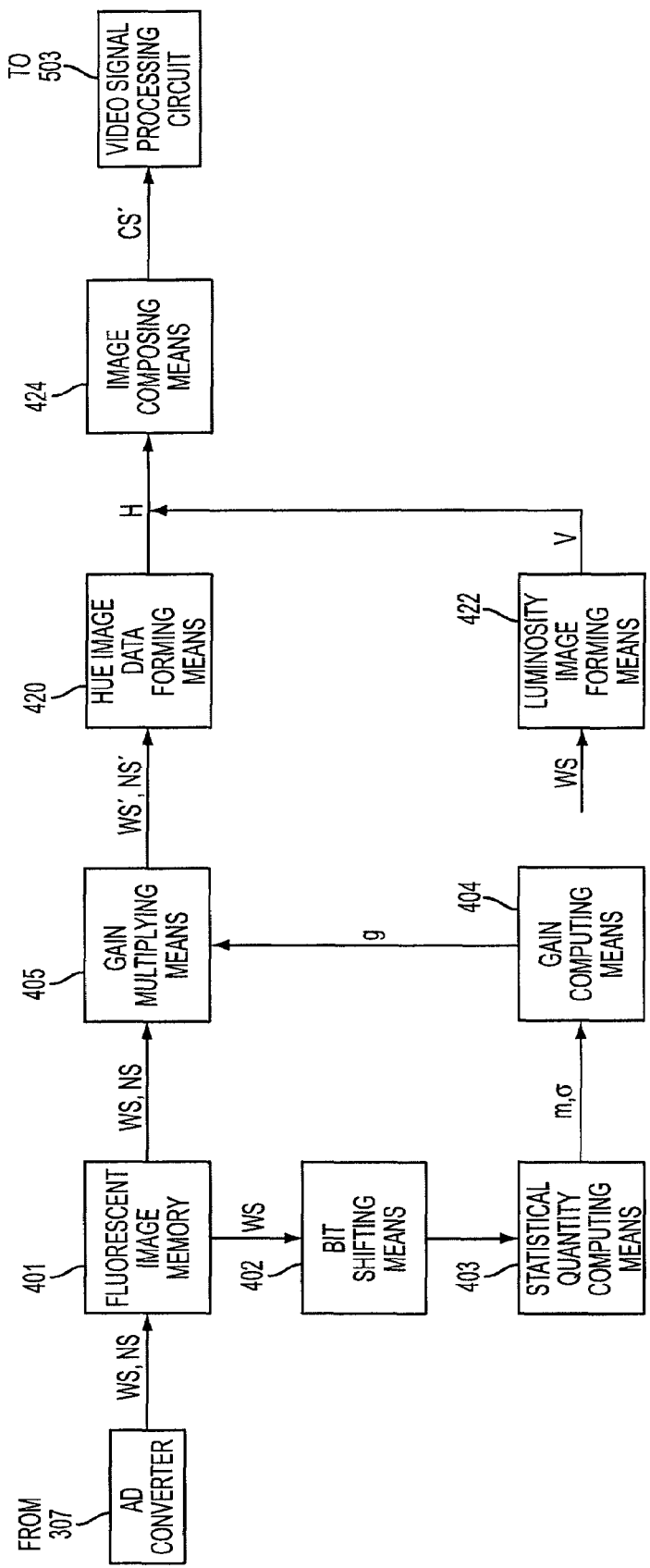
FIG. 14 is a schematic block diagram of the configuration of the image computing unit of the fluorescent endoscope according to the seventh embodiment of the present invention.

Further, according to the fifth and sixth embodiments, although the luminosity image data V has been formed, based on the wide band fluorescent image data WS', which has been multiplied by the gain g, by the luminosity image data forming means 422, the luminosity image data V can be formed based on the wide band fluorescent image data WS, which has not yet been multiplied by the gain g, as per the seventh embodiment shown in FIG. 14. In this case, it is preferable that it be possible to switch the data from which the luminosity image data V is to be formed between the image data prior to the multiplication thereof by the gain g or the image data which has been multiplied by the gain g.

Here, in the case of forming the luminosity image data V from the wide band fluorescent image data WS', which has been multiplied by the gain g, if there is a large amount of variation in the distance between the target subject 50 and the distal end of the endoscope insertion portion 100, because there is a corresponding large amount of change in the gain, the brightness of the displayed composite image also varies a large amount. Therefore, by forming the luminosity image data V based on the wide band fluorescent image data WS, which has not yet been multiplied by the gain g, the aforementioned large variations of the brightness of the displayed composite image can be prevented.

Further, according to the first through the seventh embodiments described above, although the gain g has been computed based on the statistical quantity of the wide band fluorescent image data WS, the gain g can also be computed based on the narrow band fluorescent image data NS.

Next, an endoscope implementing the fluorescence image obtaining apparatus according to the eighth embodiment of the present invention will be explained. According to the endoscope implementing the fluorescence image obtaining apparatus according to the eighth embodiment: whereas in the first embodiment the gain is computed based on the statistical quantity of the wide band fluorescent image data WS, in the eighth embodiment, the gain is computed based upon the statistical quantity of the reflectance image data RS obtained from the reflectance image Zs formed from the light reflected from the target subject 50 upon the irradiation thereof by the reference light Ls.

Figure 15:
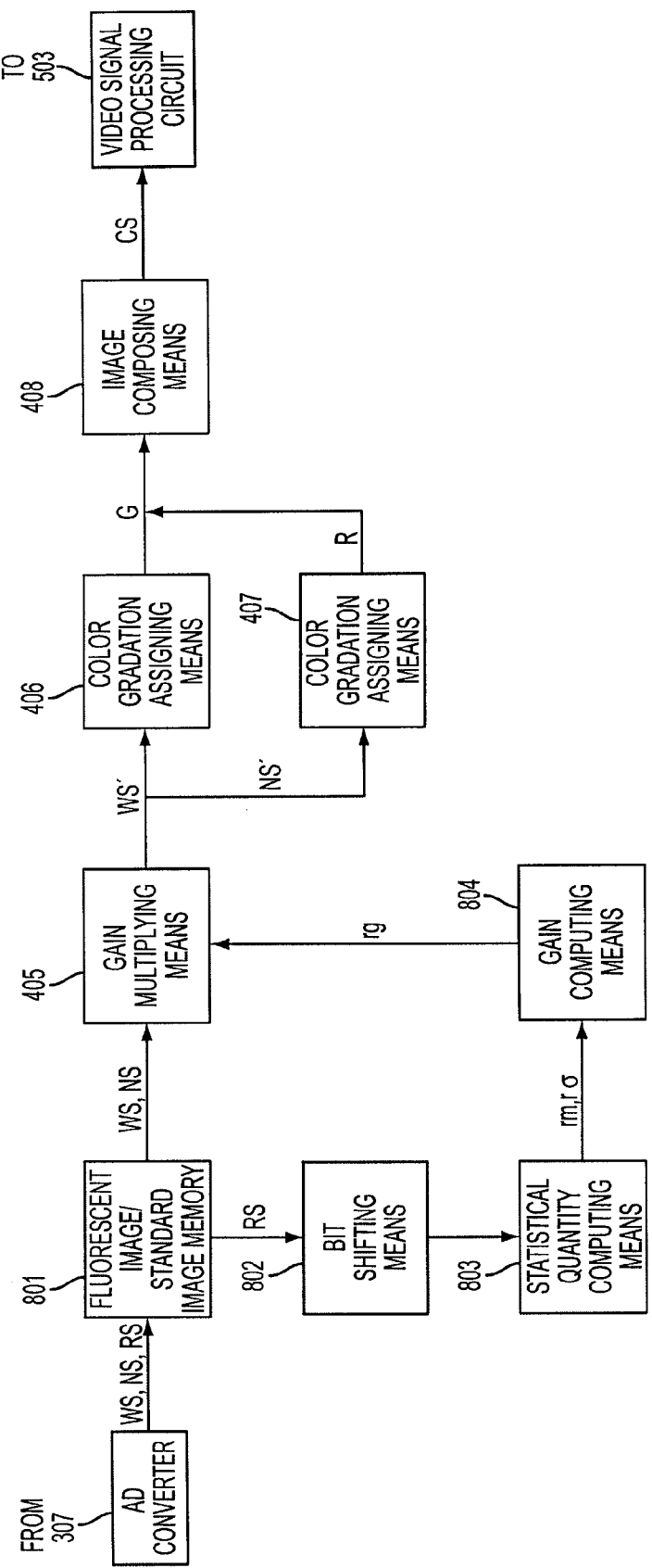
FIG. 15 is a schematic block diagram of the configuration of the image computing unit of the fluorescent endoscope according to the eighth embodiment of the present invention.

According to the configuration of the endoscope of the eighth embodiment: the optical transmitting filter 303 of the image detecting unit 300 of the first embodiment is provided as an optical transmitting filter 701; further, as shown in FIG. 15, the fluorescence image memory 401 of the image computing unit 400 is provided as a fluorescent image/standard image memory 801; further comprising a bit shifting means 802 for shifting the number of bits constituting the data of the reflectance image data RS; a statistical quantity computing means 803 for computing the statistical quantity of the bit shifted reflectance image data RS; and a gain computing means 804 for a computing a gain rg based on the statistical quantity obtained by the statistical quantity computing means 803.

Figure 16:
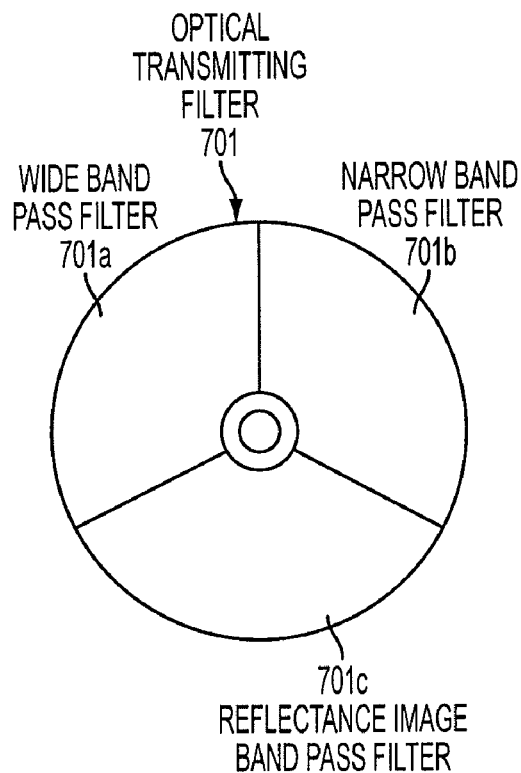
FIG. 16 is a schematic drawing of the optical transmitting filter utilized in the fluorescent endoscope according to the eighth embodiment (the second thereof)

As shown in FIG. 16, the optical transmitting filter 701 is formed of three types of band pass filters: 701a, 701b, and 701c. The band pass filter 701a is a band pass filter for transmitting a wide band fluorescent image formed of fluorescent light having wavelengths in the 430-730 nm wavelength band. The band pass filter 701b is a band pass filter for transmitting a narrow band fluorescent image formed of fluorescent light having wavelengths in the 430-530 nm wavelength band. The band pass filter 701c is a band-pass filter for transmitting a reflectance image formed of light having wavelengths in the 750-900 nm wavelength band.

Further, the fluorescent image/standard image memory 801 comprises a wide band fluorescence image recording region, a narrow band fluorescence image recording region, and a reflectance image recording region: the fluorescence images transmitted by the band pass filters 701a, 701b are stored in the respective wide band fluorescence image recording region and narrow band fluorescence image recording region; and the reflectance image transmitted by the band pass filter 701c is stored in the reflectance image recording region.

The statistical quantity computing means 803 computes the average value rm and the standard deviation rσ of each pixel of the reflectance image represented by the reflectance image data RS. Then, the average value rm and the standard deviation rσ are inputted to the gain computing means 804, and the gain rg is computed according to the following Formula (6).

$$\text{Gain upper limit} = f(DR \times a/(rm + b \times r\sigma)) \quad (6)$$

Figure 17:
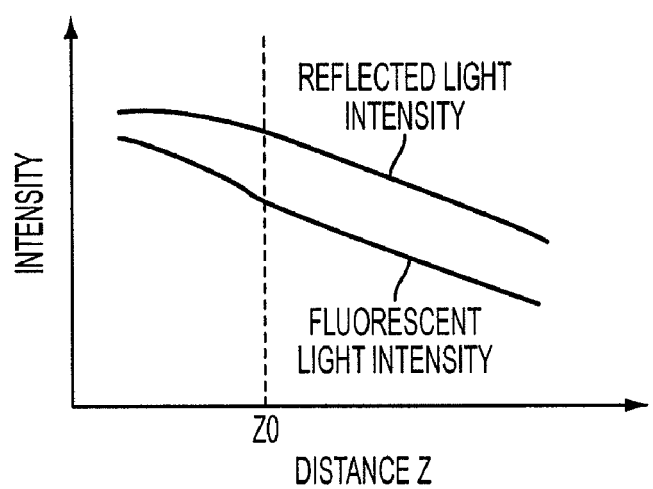
FIG. 17 is a drawing illustrating the computation of the gain.

The function f (x) is a correction function reflecting the intensity ratio of the reflected light intensity (i.e., the value of the reflectance image data RS) and the fluorescent light intensity (i.e., the values of the wide band fluorescence image data WS and the narrow band fluorescence image data NS). FIG. 17 is a graph illustrating the relation of the distance between the target subject 50 and the distal end of the endoscope insertion portion 100 and the intensity of the reflectance and fluorescence images. Because the distal end portion of the light guide 101 is formed as two eyelets, the intensity of the reflectance and fluorescence light is reduced non-linearly up until the distance z from the target subject 50 becomes z0, as shown in FIG. 17; at a distance larger than z0, the intensity of the reflectance and fluorescence light is reduced in inverse proportion to the square of the distance z. This is due to the fact that although the merging of the light emitted from two locations occurs according to a gaussian distribution if the distance z is greater than or equal to z0, for cases in which the distance z is less than z0, the merging of the light emitted from two locations does not occur according to a gaussian distribution.

Therefore, for cases in which the gain rg is computed based on the reflectance image data RS, the manner in which the distribution of the pixel values of the fluorescence and reflectance images which have been multiplied by said gain rg changes is such that said change differs in accordance to the length, short or long, of the distance z.

Accordingly, in a case, for example, in which f(x)=px, at locations for which the distance is short, the change in distribution becomes expressed by a variable (e.g., a value that approaches 1 as the distance z becomes shorter); by setting the coefficient p so that it is a constant at locations for which the distance is long, a gain rg in which the change to the correction function due to the distance z is reduced can be obtained. Note that because it is not possible to detect the distance z directly, the value of the coefficient p can be determined based upon the value of the reflectance image data RS. That is to say, when the data value of the reflectance image data RS is large, the coefficient p is set as a value close to 1; when the data value is small, the coefficient p can be a value computed based on the ratio of the fluorescent images and the reflectance image.

Note that by obtaining the maximum value (Max) and the minimum value (Min) of each pixel of the wide band fluorescence image, the gain rg may also be computed by use of the following equation (7). In addition, the gain rg may be computed based solely on the pixel values for a desired region of the reflectance image (e.g., a region of the image that warrants observation with particular attention).

$$\text{Gain upper limit} = f[DR \times a / \{(r\text{Max} + r\text{Min})/2 + b \times (r\text{Max} - r\text{Min})/2\} \quad (7)$$

Hereinafter, the operation of the eighth embodiment will be explained. According to the eighth embodiment: the filter rotating means 304 is driven based on a signal from the control computer 200, and after the fluorescent image Zj has passed through the band pass filter 701a, said fluorescent image Zj is focused by the fluorescent light focusing lens 305 and obtained as a wide band fluorescent image by the high sensitivity fluorescence image obtaining element 306. Further, after the fluorescent image Zj has passed through the band pass filter 701b, said fluorescent image Zj is focused by the fluorescent light focusing lens 305 and obtained as a narrow band fluorescent image by the high sensitivity fluorescence image obtaining element 306. The visible image signals from the high sensitivity fluorescence image obtaining element 306 are inputted to the AD converter 307, and after being digitized therein, are stored as a wide band fluorescent image data WS and a narrow band fluorescent image data NS in the respective wide band fluorescent image recording region and narrow band fluorescent image recording region of the reflectance image/fluorescent image memory 801.

On the other hand, when a reflectance image is to be obtained: first, based on a control signal from the control computer 200, the white light source power source 115 is activated and white light Lw is emitted. The white light Lw contains reference light Ls having wavelengths from 750-900 nm. The white light Lw enters the white light guide 101b via the white light focusing lens 116, and after being guided to the distal end of the endoscope insertion portion 100, said white light Lw is emitted onto the target subject 50 from the illuminating lens 104.

The light reflected from the target subject 50 upon the irradiation thereof by the white light Lw is focused by the focusing lens 106, enters the distal end of the image fiber 103, and enters the excitation light cutoff filter 302 via the image fiber 103. The reflectance image Zs that has passed through the excitation light cutoff filter 302 enters the optical transmitting filter 303.

The filter rotating means 304 is driven, based on a signal from the control computer 200, and after the reflectance image Zs has passed through the band pass filter 701c, said reflectance image Zs is focused by the fluorescent light focusing lens 305 and obtained as a standard image by the high sensitivity fluorescence image obtaining element 306. The visible image signal from the high sensitivity fluorescence image obtaining element 306 is inputted to the AD converter 307, and after being digitized therein, is stored as a standard image data RS in the reflectance image recording region of the reflectance image/fluorescent image memory 801.

The standard image data RS stored in the reflectance image/fluorescent image memory 801 is inputted to the statistical quantity computing means 803 after being bit shifted by the bit shifting means 802 so as to be represented by 8-bit data. The statistical quantity computing means 803 computes the statistical quantity. The statistical quantity is inputted to the gain computing means 804, and the gain computing means 804 computes the gain rg based on said statistical quantity. Then, in the same manner as in the first embodiment, the wide band fluorescent image data WS and the narrow band fluorescent image data NS are multiplied by the gain g to obtain a wide band fluorescent image data WS' and a narrow band fluorescent image data NS'. Further, a G color gradation is assigned to the wide band fluorescent image data WS' and an R color gradation is assigned to the narrow band fluorescent image data NS'; these two colorized wide band fluorescent image data WS' and narrow band fluorescent image data NS' are then combined to obtain a composite image data CS.

Here, the intensity of the light reflected from the target subject 50 upon the irradiation thereof by the reference light Ls is larger than the intensity of the wide band fluorescent light emitted from the target subject 50 upon the irradiation thereof by the excitation light. Therefore, the computation of the gain rg, based on the statistical quantity, can be performed more advantageously in comparison to the first embodiment; whereby the distinguishability of the tissue state of the target subject 50 appearing in the composite image formed according to the current embodiment can be improved a level.

Figure 18:
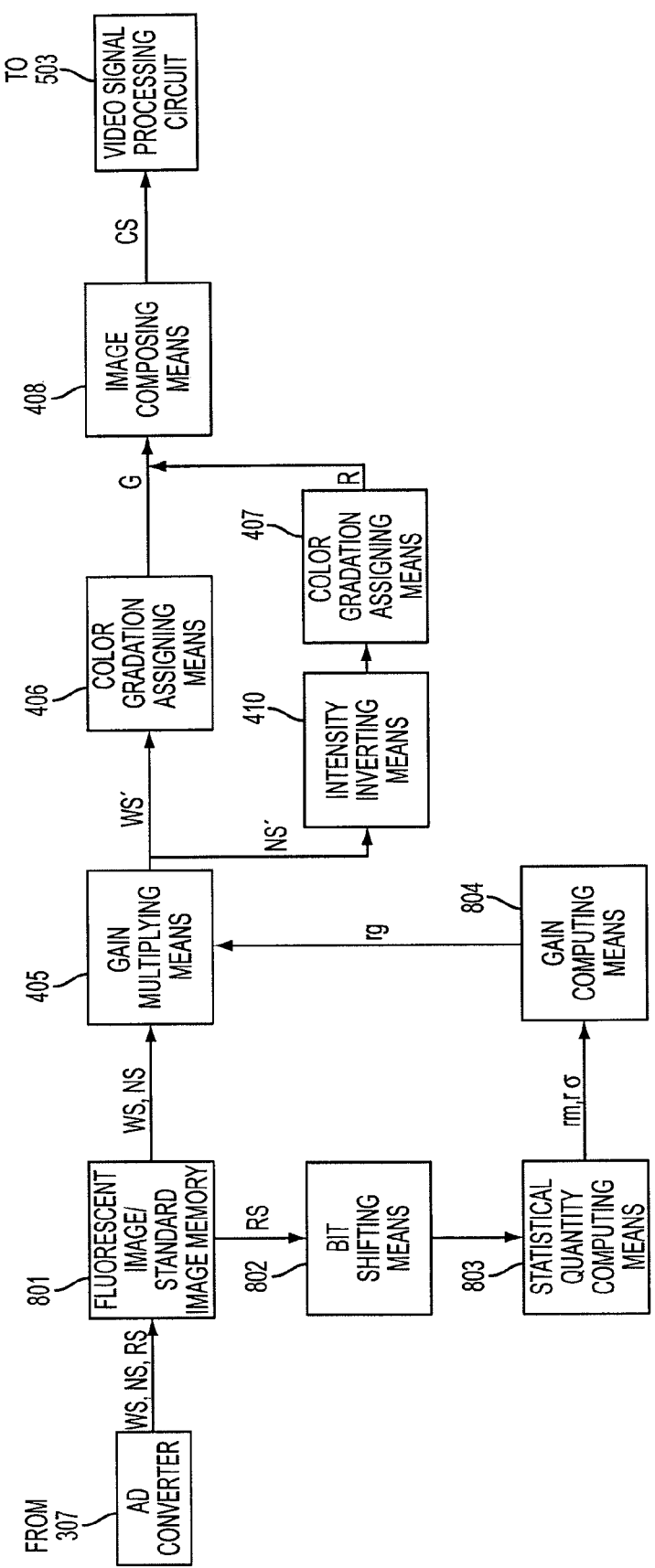
FIG. 18 is a schematic block diagram of the configuration of the image computing unit of the fluorescent endoscope according to the ninth embodiment of the present invention.

Next, an endoscope implementing the fluorescence image obtaining apparatus according to the ninth embodiment of the present invention will be explained. According to the endoscope implementing the fluorescence image obtaining apparatus according to the ninth embodiment: the image computing unit 400 of the eighth embodiment inverts the intensity of the narrow band fluorescent image data NS', which has been multiplied by the gain rg, to obtain a reverse narrow band fluorescent image data NS" as in the second embodiment; and assigns a R color gradation to the reverse narrow band fluorescent image data NS". Therefore, as shown in FIG. 18, the image computing unit 400 of the endoscope according to the ninth embodiment is provided with an intensity inverting means 410 for inverting the intensity of the narrow band fluorescent image data NS', which has been multiplied by the gain rg.

Hereinafter the operation of the ninth embodiment will be explained. Note that because the processes up until the multiplication of the fluorescent image data by the gain rg are the same as those of the first embodiment, further explanation thereof has been omitted. According to the ninth embodiment: the gain rg is computed based on the reflectance image data RS; the narrow band fluorescent image data NS is multiplied by the gain rg to obtain a narrow band fluorescent image data NS'; the narrow band fluorescent image data NS' is inputted to the intensity inverting means 410; the intensity inverting means 410 inverts the intensity of the narrow band fluorescent image data NS' to obtain a reverse narrow band fluorescent image data NS", assigns an R color gradation to the reverse narrow band fluorescent image data NS", and then combines the reverse narrow band fluorescent image data NS" and the wide band fluorescence image data WS', to which a green color gradation has been assigned, to obtain a composite image data CS.

In this manner, by inverting the intensity of the narrow band fluorescent image data NS', the difference between the normal tissue and the diseased tissue appearing in the composite image can be rendered more clearly, whereby the distinguishability of the tissue state of the target subject can be improved a level.

Figure 19:
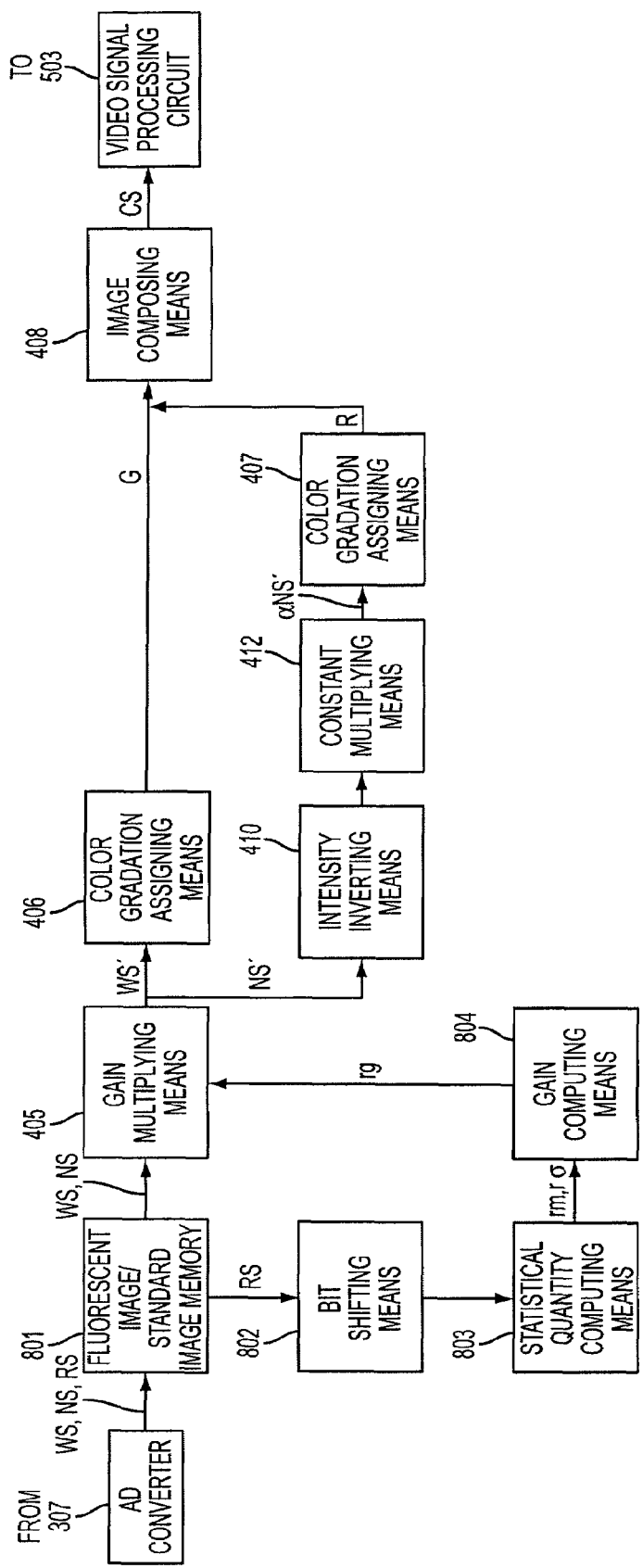
FIG. 19 is a schematic block diagram of the configuration of the image computing unit of the fluorescent endoscope according to the tenth embodiment of the present invention.

Next, an endoscope implementing the fluorescence image obtaining apparatus according to the tenth embodiment of the present invention will be explained. According to the endoscope implementing the fluorescence image obtaining apparatus according to the tenth embodiment: the image computing unit 400 of the ninth embodiment inverts the intensity of the narrow band fluorescent image data NS', which has been multiplied by the gain rg, to obtain a reverse narrow band fluorescent image data NS''; then, multiplies the reverse narrow band fluorescent image data NS'' by a predetermined constant α (α>1) to obtain a constant-multiplied reverse narrow band fluorescent image data NS''; and assigns a R color gradation to the constant-multiplied reverse narrow band fluorescent image data NS'', which has been multiplied by the constant α has been multiplied. Therefore, as shown in FIG. 19, the image computing unit 400 of the endoscope according to the tenth embodiment comprises a constant multiplying means 412, which is the same as that of the third embodiment.

Hereinafter the operation of the tenth embodiment will be explained. Note that because the processes up until the multiplication of the fluorescent image data by the gain g are the same as those of the first embodiment, further explanation thereof has been omitted. According to the tenth embodiment: the gain rg is computed based on the reflectance image data RS; the narrow band fluorescent image data NS is multiplied by the gain rg to obtain a narrow band fluorescent image data NS', which has been multiplied by the gain rg; the narrow band fluorescent image data NS' is inputted to the intensity inverting mean 410; and the intensity inverting means 410 inverts the intensity of the narrow band fluorescent image data NS' to obtain a reverse narrow band fluorescent image data NS''. Then, the reverse narrow band fluorescent image data NS'' is inputted to the constant multiplying means 412. The constant multiplying means 412 multiplies the reverse narrow band fluorescent image data NS'' by a predetermined constant α to obtain a constant-multiplied reverse narrow band fluorescent image data NS''; assigns an R color gradation to the reverse narrow band fluorescent image data NS''; and combines this colorized constant-multiplied reverse narrow band fluorescent image data NS'' and the wide band fluorescence image data WS', to which a green color gradation has been assigned, to obtain a composite image data CS.

In this manner, by multiplying the reverse narrow band fluorescent image data NS'' by a constant α, the effect wherein the dark portions appearing in the composite image also become red in color can be suppressed the same as in the third embodiment, preventing the misrecognition of portions that are simply dark and diseased tissue, and improving the distinguishability of the tissue state by a level.

Note that according to the ninth an tenth embodiments, the intensity of the narrow band fluorescent image data NS' has been inverted; however, the intensity of the wide band fluorescent image data WS' may be inverted instead.

Figure 20:
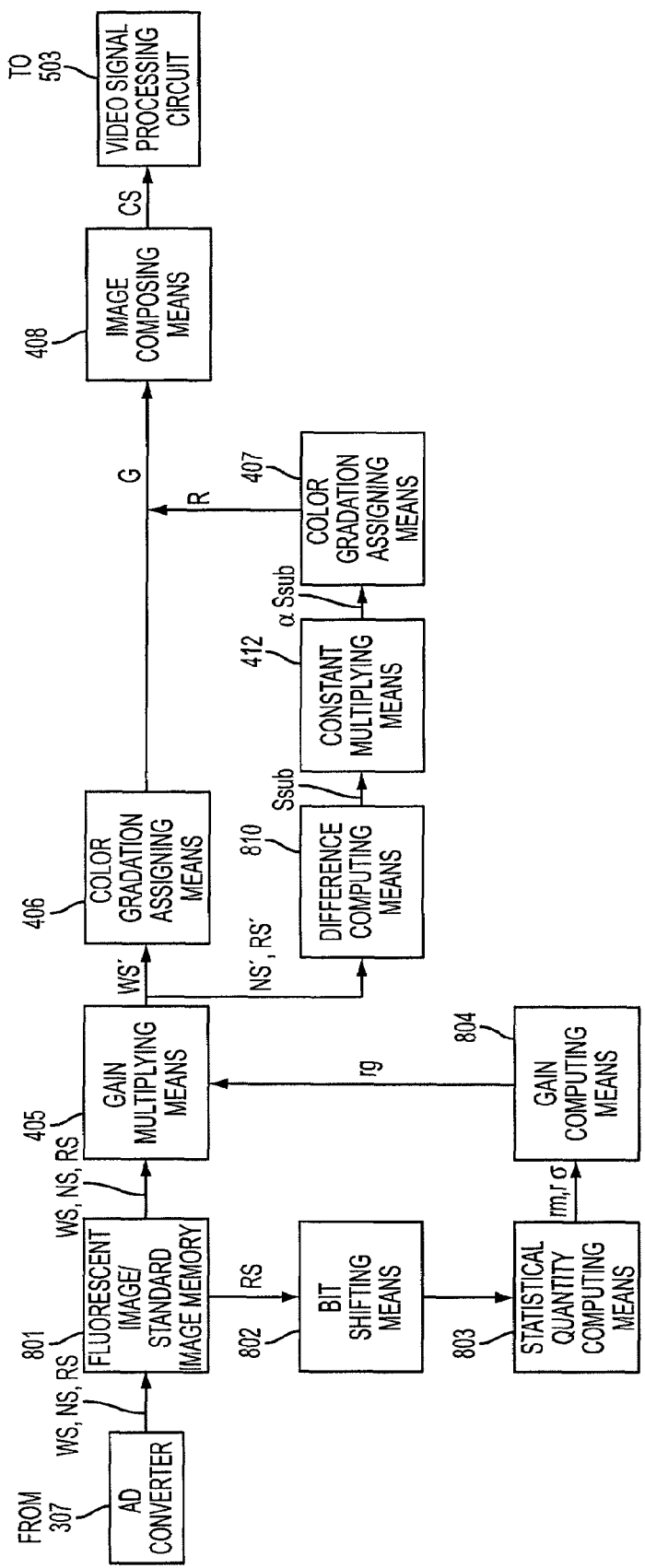
FIG. 20 is a schematic block diagram of the configuration of the image computing unit of the fluorescent endoscope according to the eleventh embodiment of the present invention.
Figure 21:
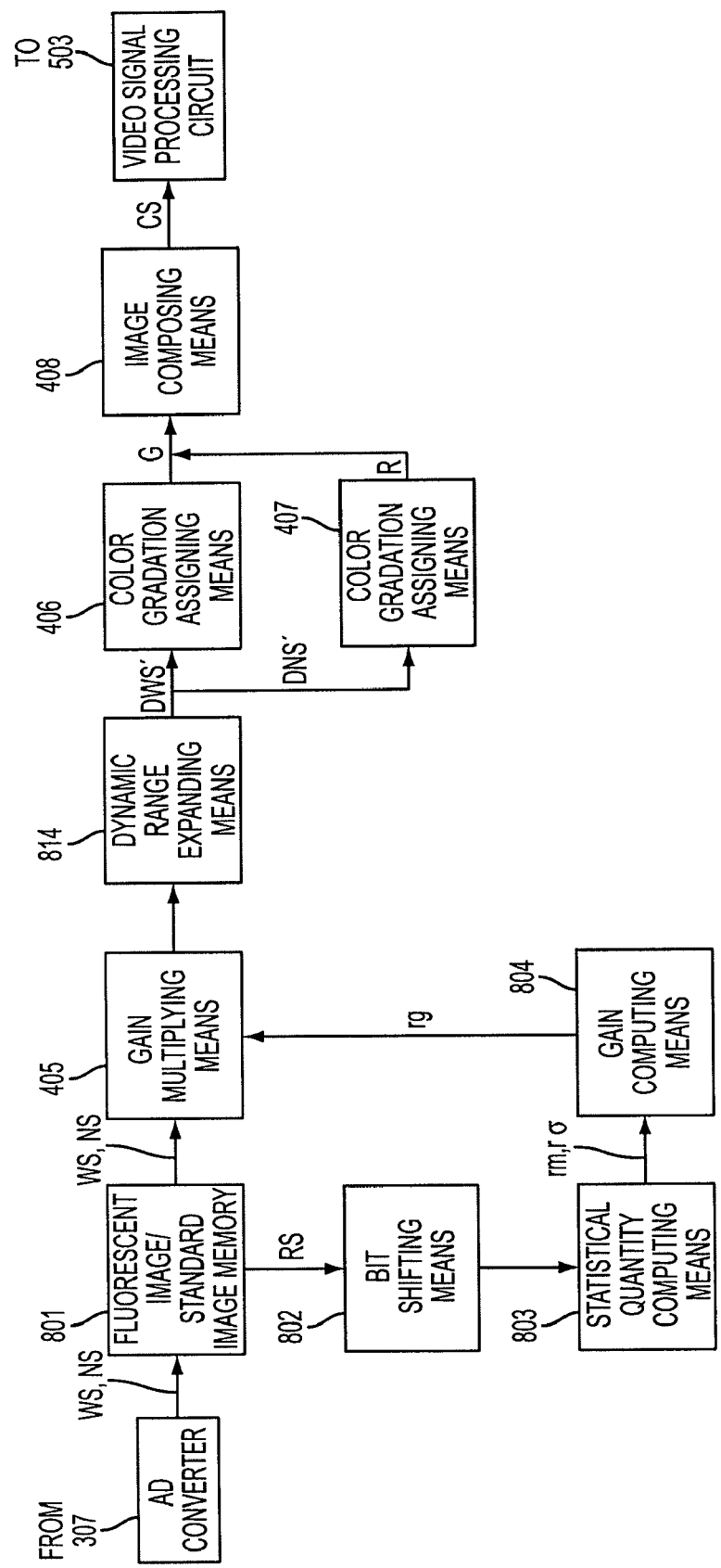
FIG. 21 is a schematic block diagram of the configuration of the image computing unit of the fluorescent endoscope according to the twelfth embodiment of the present invention.

Next, an endoscope implementing the fluorescence image obtaining apparatus according to the eleventh embodiment of the present invention will be explained. According to the endoscope implementing the fluorescence image obtaining apparatus according to the eleventh embodiment: the gain multiplying means 405 multiplies the narrow band fluorescent image data NS and the reflectance image data RS by the gain rg to obtain a narrow band fluorescent image data NS' and a reflectance image data RS'; computes the difference data between the narrow band fluorescent image data NS' and a reflectance image data RS'; then, multiplies the difference data by a predetermined constant α and assigns an R color gradation to the product obtained thereby. Therefore, as shown in FIG. 20, the image computing unit 400 of the endoscope according to the eleventh embodiment comprises a difference data computing means for computing the difference data Ssub between the narrow band fluorescent image data NS', which has been multiplied by the gain rg, and the reflectance image data RS', which has been multiplied by the gain rg, and a constant multiplying means 412, which is the same as that of the third embodiment.

The difference computing means 810 computes the difference between the values of the corresponding pixels of the reflectance image represented by the reflectance image data RS', which has been multiplied by the gain rg, and the fluorescent image represented by the narrow band fluorescent image data NS', which has been multiplied by the gain rg, to obtain a difference data Ssub.

Hereinafter the operation of the eleventh embodiment will be explained. Note that because the processes up until the multiplication of the fluorescent image data by the gain g are the same as those of the first embodiment, further explanation thereof has been omitted. According to the eleventh embodiment: the gain rg is computed based on the reflectance image data RS; the reflectance image represented by the reflectance image data RS is multiplied by the gain rg to obtain reflectance image data RS', the narrow band fluorescent image data NS is multiplied by the gain rg to obtain narrow band fluorescent image data NS'; the reflectance image data RS' and narrow band fluorescent image data NS' are inputted to the difference computing means 810; and the difference computing means 810 computes difference data Ssub. Further, the constant multiplying means 412 multiplies the difference data Ssub by the constant α to obtain an α Ssub, and assigns an R color gradation to the α Ssub. Next, the R colorized α Ssub and the wide band fluorescence image data WS', to which a green color gradation has been assigned, are combined to obtain a composite image data CS.

In this manner, by computing the Ssub of the reflectance image represented by the reflectance image data RS', which has been multiplied by the gain rg, and the narrow band fluorescent image data NS', which has been multiplied by the gain rg, the difference between the diseased tissue and the normal tissue can be more clearly rendered. That is to say, by adjusting the luminosity of the fluorescence image, which is an effect of the intensity of the fluorescent light, to within a desired luminosity range, the distinguishability of the tissue state of the target subject can be improved.

Next, an endoscope implementing the fluorescence image obtaining apparatus according to the twelfth embodiment of the present invention will be explained. According to the endoscope implementing the fluorescence image obtaining apparatus according to the twelfth embodiment: the narrow band fluorescent image data NS' and the wide band fluorescent image data WS', which have been multiplied by the gain rg, as in the eighth embodiment, are subjected to a dynamic range expansion process, based on the statistical quantity computed by the statistical quantity computing means 803, to obtain a wide band fluorescence image data DWS' and a narrow band fluorescent image data DNS'. Therefore, as shown in FIG. 20, the image computing unit 400 of the endoscope according to the twelfth embodiment is provided with a dynamic range expanding means 814, which is the same as that of the fourth embodiment.

As shown in the formula (8) below, the dynamic range expanding means 814 computes, based on the average value m and the standard deviation σ of each pixel of the reflectance image computed by the statistical quantity computing means 803, the distribution range of the pixel values of each fluorescence image represented by the wide band fluorescence image data DWS' and the narrow band fluorescent image data DNS', which have been subjected to the dynamic range expansion process. Note that in the Formula (8), b=2, for example.

$$\text{Distribution range} = rm - b \times r\sigma \text{ to } rm + b \times r\sigma \qquad (8)$$

Then, if the minimum value (Min) is designated as rm−b×rσ, the maximum value (Max) as rm+b×rσ, each pixel value of each fluorescent image that has been subjected to the dynamic range expansion process can be computed by use of the function rg (x) (where x equals the pixel values of the narrow band fluorescent image and the wide band fluorescent image which have been multiplied by the gain rg) shown in the Formula (9) below.

$$rg(x) = (x - \text{Min})/(\text{Max} - \text{Min}) \qquad (9)$$

Hereinafter the operation of the twelfth embodiment will be explained. Note that because the processes up until the multiplication of the fluorescent image data by the gain g are the same as those of the first embodiment, further explanation thereof has been omitted. According to the twelfth embodiment: the gain g is computed based on the reflectance image data RS; the narrow band fluorescent image data NS and the wide band fluorescence image data WS are multiplied by the gain g to obtain a narrow band fluorescent image data NS' and a wide band fluorescent image data WS'; the narrow band fluorescent image data NS' and the wide band fluorescence image data WS' are inputted to the dynamic range expanding means 814, and are subjected to the dynamic range expansion process therein to obtain a the wide band fluorescence image data DWS' and a narrow band fluorescent image data DNS'. The wide band fluorescence image data DWS' and the narrow band fluorescent image data DNS' are assigned an R color gradation and a G color gradation, respectively, and are then combined to obtain a composite image data CS.

In this manner, by expanding the dynamic range of the narrow band fluorescent image data NS' and the wide band fluorescent image data WS', because the contrast of the composite image formed thereof can be made higher, the change in the tissue state of the target subject 50 can be represented more accurately in the composite image, whereby the distinguishability of the tissue state of the target subject 50 can be further improved.

Note that for cases in which the statistical quantity computing means 803 computes the Max and Min values of each pixel of the reflectance image, the dynamic range expanding means 814 can compute the distribution range of the pixel values of each respective dynamic-range expanded fluorescent image represented by the wide band fluorescence image data DWS' and the narrow band fluorescent image data DNS', by use of the Formula (10) below. Note that in Formula (10), c and d are arbitrary constants.

$$\text{Distribution range} = (r\text{Max} + r\text{Min})/2 - c \times (r\text{Max} - r\text{Min})/2 \text{ to } (r\text{Max} + r\text{Min})/2 + d \times (r\text{Max} - r\text{Min})/2 \qquad (10)$$

Note that according to the twelfth embodiment, the dynamic expansion process can be preset so as to be performed for each image, or can be performed only when so desired by the operator of the endoscope, by use of a foot switch 210 or a hand operated switch 212, in the same manner as in the fourth embodiment.

Further, according to the twelfth embodiment described above, the dynamic range expanding means 814 of the eighth embodiment has been provided, and the dynamic range process performed; however, it is also possible to perform the same dynamic range process in the ninth through the eleventh embodiments. In this case, according to the ninth embodiment, the dynamic range expansion process can be performed on the reverse narrow band fluorescent image data NS'; in the tenth embodiment, the dynamic range expansion process can be performed on the constant-multiplied reverse narrow band fluorescent image data NS'. Further, according to the eleventh embodiment, the dynamic range expansion process can be performed on the constant-multiplied difference data α Ssub.

Note that according to the eighth through the twelfth embodiments described above, a G color gradation has been assigned to the wide band fluorescence image data WS' (included those of which the dynamic range has been expanded) and an R color gradation has been assigned to the narrow band fluorescent image data NS' (included those of which the dynamic range has been expanded, those of which the intensity thereof has been inverted, and those that have been multiplied by the constant α) or to the constant-multiplied difference data α Ssub; however, an R color gradation can be assigned to the wide band fluorescence image data WS', and a G color gradation can be assigned to the narrow band fluorescent image data NS' or the constant-multiplied difference data α Ssub. Further, in addition to the G and R color gradations, a B color gradation maybe assigned as well. In this case, a G and a B color gradation can be assigned to the wide band fluorescence image data WS', and an R color gradation can be assigned to the narrow-band fluorescent image data NS' or the constant-multiplied difference data α Ssub; alternatively, a G and a B color gradation can be assigned to the narrow band fluorescence image data NS' or the constant-multiplied difference data α Ssub, and an R color gradation can be assigned to the wide band fluorescent image data WS'. Note that the change in the assignment of the color gradations can be performed after the fluorescent images and the constant-multiplied difference data α Ssub have been subjected to the dynamic range expansion process, the of the constant α multiplication process, or the intensity inversion process.

Figure 22:
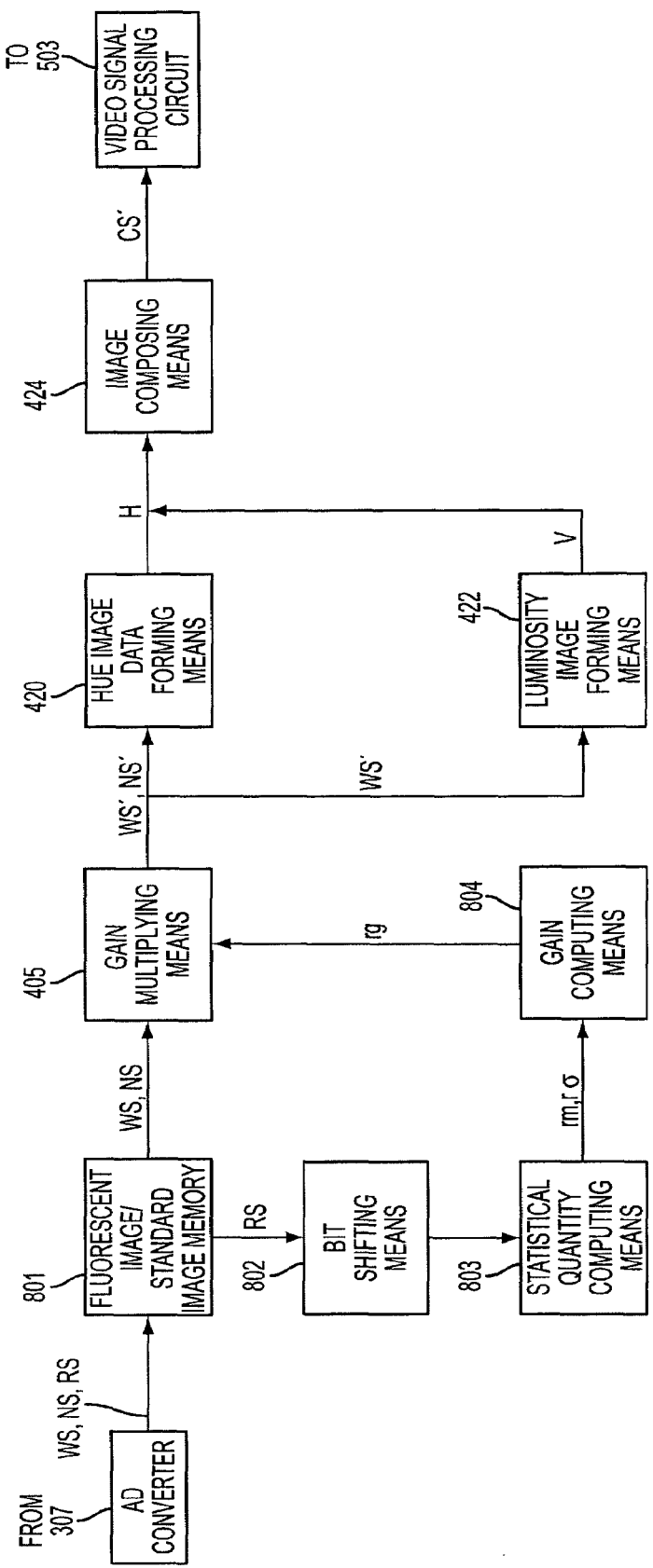
FIG. 22 is a schematic block diagram of the configuration of the image computing unit of the fluorescent endoscope according to the thirteenth embodiment of the present invention.

Next, an endoscope implementing the fluorescence image obtaining apparatus according to the thirteenth embodiment of the present invention will be explained. According to the endoscope implementing the fluorescence image obtaining apparatus according to the thirteenth embodiment: a hue image data H is obtained of the narrow band fluorescent image data NS' and the wide band fluorescent image data WS', which have been multiplied by the gain rg, as in the eighth embodiment, a luminosity image data V is obtained of the wide band fluorescent image data WS', and the hue image data H and the luminosity image data V are combined to obtain a composite image data. Therefore, as shown in FIG. 22, the image computing unit 400 of the endoscope according to the thirteenth embodiment comprises, in a configuration similar to that of the fifth embodiment: a hue image data forming means 420, instead of a hue gradation assigning means 406, a hue gradation assigning means 407 and an image composing means 408, for forming a hue data H, which represents a hue, from the narrow band fluorescent image data NS' and the wide band fluorescent image data WS', which have been multiplied by the gain rg; a luminosity image data forming means 422 for forming, based on the wide band fluorescent image data WS', a luminosity image data V representing a brightness; and an image composing means 424 for combining the hue data H and the luminosity image data V to obtain a composite image data CS'.

Hereinafter the operation of the thirteenth embodiment will be explained. Note that because the processes up until the multiplication of the fluorescent image data by the gain g are the same as those of the eighth embodiment, further explanation thereof has been omitted. According to the thirteenth embodiment: the narrow band fluorescent image data NS' and the wide band fluorescence image data WS', which have been multiplied by the gain rg formed based on the reflectance image data RS, are inputted to the hue image data forming means 420. The hue image data forming means 420 outputs the wide band fluorescent image data WS' and the narrow band fluorescent image data NS' to respectively different color planes (e.g., G and R), and forms, based on the additive color mixture method, a color added and mixed image data representing a color added and mixed image ; then, by computing, based on this color added and mixed image data, the hue value of the color added and mixed image represented by said color added and mixed image data and occurring in the Munsell color system, the hue image data forming means 420 forms a hue data value H.

On the other hand, the wide band fluorescent image data WS', which has been multiplied by the gain rg, is inputted to the luminosity image data forming means 422; then, the luminosity image data forming means forms, based on the range of the pixel values of the wide band fluorescent image data represented by the wide band fluorescent image data WS' and the look-up table, a luminosity image data V determining a luminosity V (Value) occurring in the Munsell color system.

The hue image data H and the luminosity image data V are inputted to the image composing means 424, and the image composing means 424 forms a composite image data CS'. In this case, because a saturation is required in addition to the hue and luminosity, when the composite image CS' is to be composed, the largest value of each hue and each luminosity is set as a saturation value S occurring in the Munsell color system, and the composite image data CS' is formed by performing an RGB conversion process. In this manner, data relating to the tissue state of the target subject 50 as well as data relating to the form of the target subject 50 can be displayed concurrently in a single image, the same as in the fifth embodiment.

Figure 23:
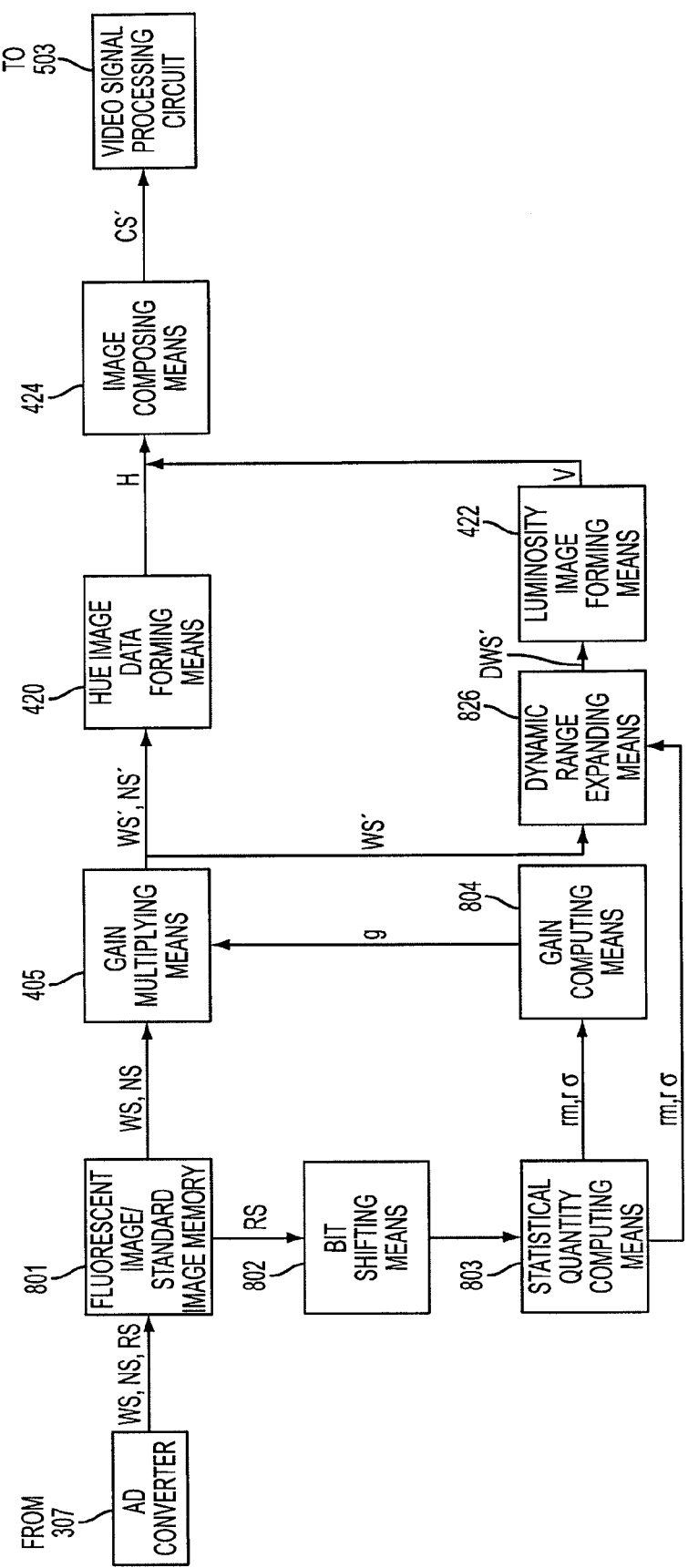
FIG. 23 is a schematic block diagram of the configuration of the image computing unit of the fluorescent endoscope according to the fourteenth embodiment of the present invention.

Next, an endoscope implementing the fluorescence image obtaining apparatus according to the fourteenth embodiment of the present invention will be explained. According to the endoscope implementing the fluorescence image obtaining apparatus according to the fourteenth embodiments the narrow band fluorescent image data NS' and the wide band fluorescent image data WS', which have been multiplied by the gain rg formed based on the reflectance image data RS, as in the thirteenth embodiment, are subjected to a dynamic range expansion process, based on the statistical quantity computed by the statistical quantity computing means 803. Therefore, as shown in FIG. 23, the image computing unit 400 of the endoscope according to the fourteenth embodiment is provided with a dynamic range expanding means 826 for subjecting the wide band fluorescent image data WS', which has been multiplied by said gain rg, to a dynamic range expansion process. Note that because the dynamic range expanding means 826 performs the same process as that performed by the dynamic range expanding means 414 of the fourth embodiment, a detailed explanation thereof has been omitted.

In this manner, by providing the dynamic range expanding means 826, because the distribution of the luminosity image data V can be made to span substantially the entire area of the display gradation curve of the composite image monitor 602, the contrast of the composite image formed thereof can be made higher. Accordingly, the change in the tissue state of the target subject 50 can be represented more accurately in the composite image, whereby the distinguishability of the tissue state of the target subject 50 can be further improved.

Note that according to the fourteenth embodiment, the dynamic expansion process can be preset so as to be performed for each image, or can be performed only when so desired by the operator of the endoscope, by use of a foot switch 210 or a hand operated switch 212, in the same manner as occurred in the fourth embodiment.

Further, according to the above-described thirteenth and fourteenth embodiments, although hue image data H and luminosity image data V have been formed in addition to the processes performed in the eighth embodiment, it is also possible that a hue image data H and luminosity image data V be formed and combined to obtain a composite image data CS' in addition to the processes performed in the ninth through twelfth embodiments described above. In this case, according to the ninth embodiment, the hue image data H can be formed utilizing the reverse narrow band fluorescence image NS"; according to the tenth embodiment, the hue image data H can be formed utilizing the constant-multiplied reverse narrow band fluorescence image NS''. Further, according to the eleventh embodiment, the hue image data H can be formed utilizing the difference data α Ssub, which has been multiplied by the constant α; and according to the twelfth embodiment, the hue image data H can be formed utilizing the wide band fluorescence image DWS' and the narrow band fluorescence image DNS', which have been subjected to a dynamic range expansion process.

Still further, according to the above-described thirteenth and fourteenth embodiments, although the luminosity image data V has been formed, based on the wide band fluorescent image data WS', which has been multiplied by the gain rg, by the luminosity image data forming means 422, the luminosity image data V may also be formed based on the narrow band fluorescent image data NS', which has been multiplied by the gain rg.

Figure 24:
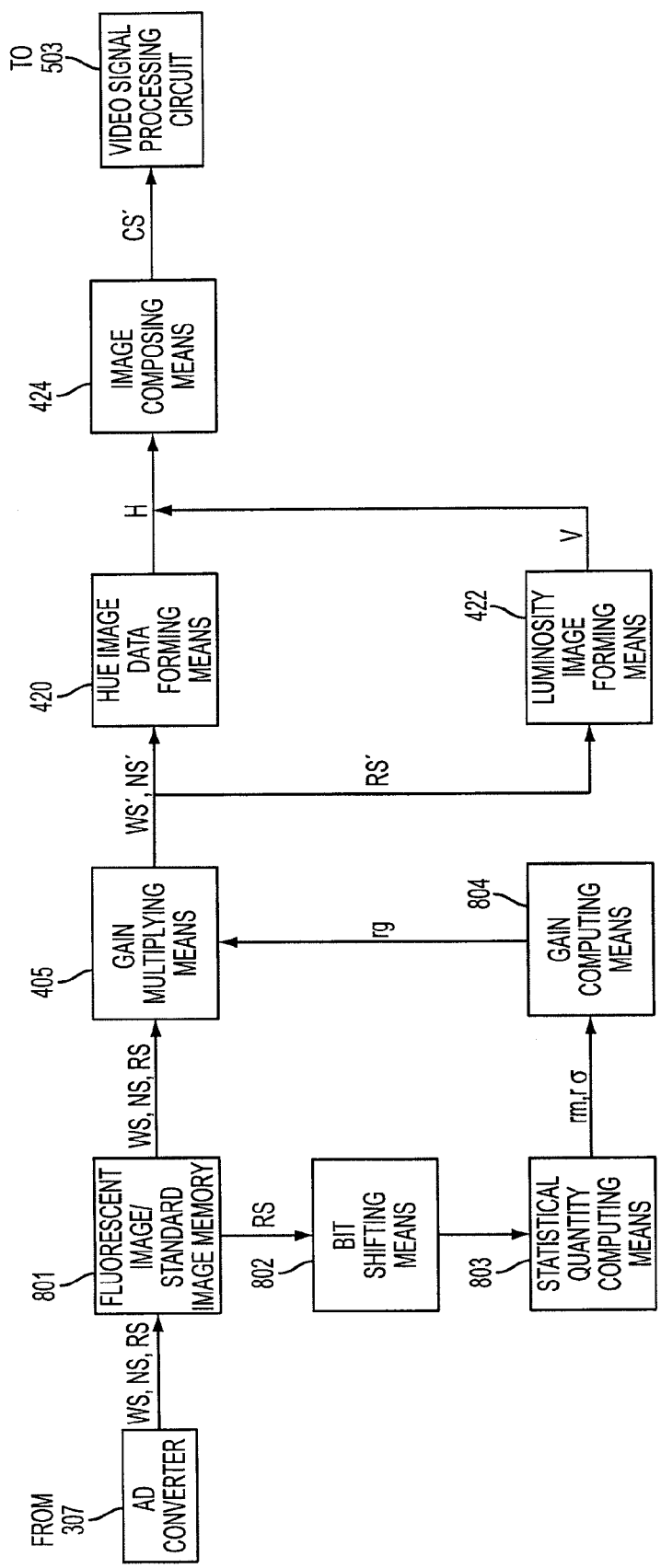
FIG. 24 is a schematic block diagram of the configuration of the image computing unit of the fluorescent endoscope according to the fifteenth embodiment of the present invention.

In addition, according to the above-described thirteenth and fourteenth embodiments, the luminosity image data V has been formed, based on the wide band fluorescent image data WS', which has been multiplied by the gain rg, by the luminosity image data forming means 422; however, according to the fifteenth embodiment shown in FIG. 24, the reflectance image data RS' may also be multiplied by the gain rg, by the gain multiplying means 405, to obtain a reflectance image data RS', which has been multiplied by the gain rg, and the luminosity image data V may also be formed based on this reflectance image data RS', which has been multiplied by the gain rg.

Figure 25:
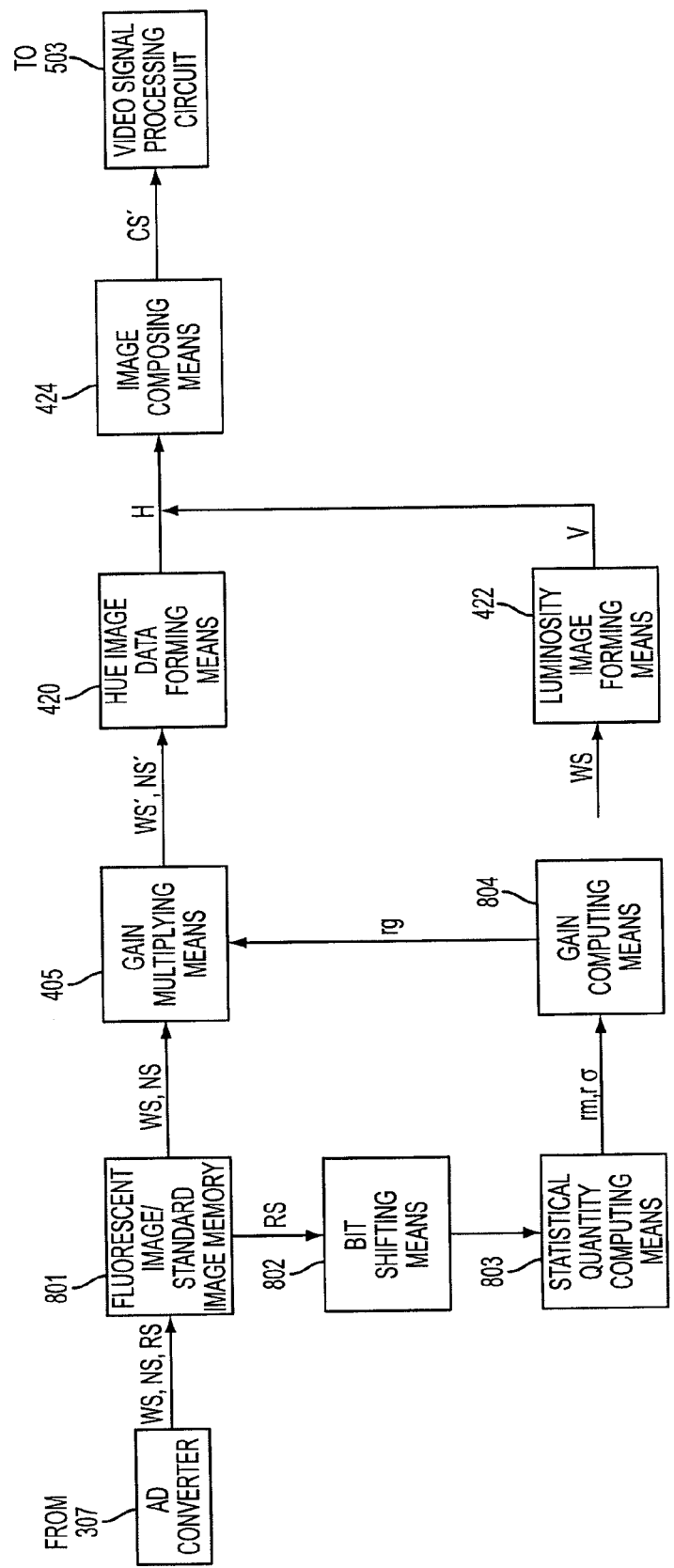
FIG. 25 is a schematic block diagram of the configuration of the image computing unit of the fluorescent endoscope according to the sixteenth embodiment of the present invention.
Figure 26:
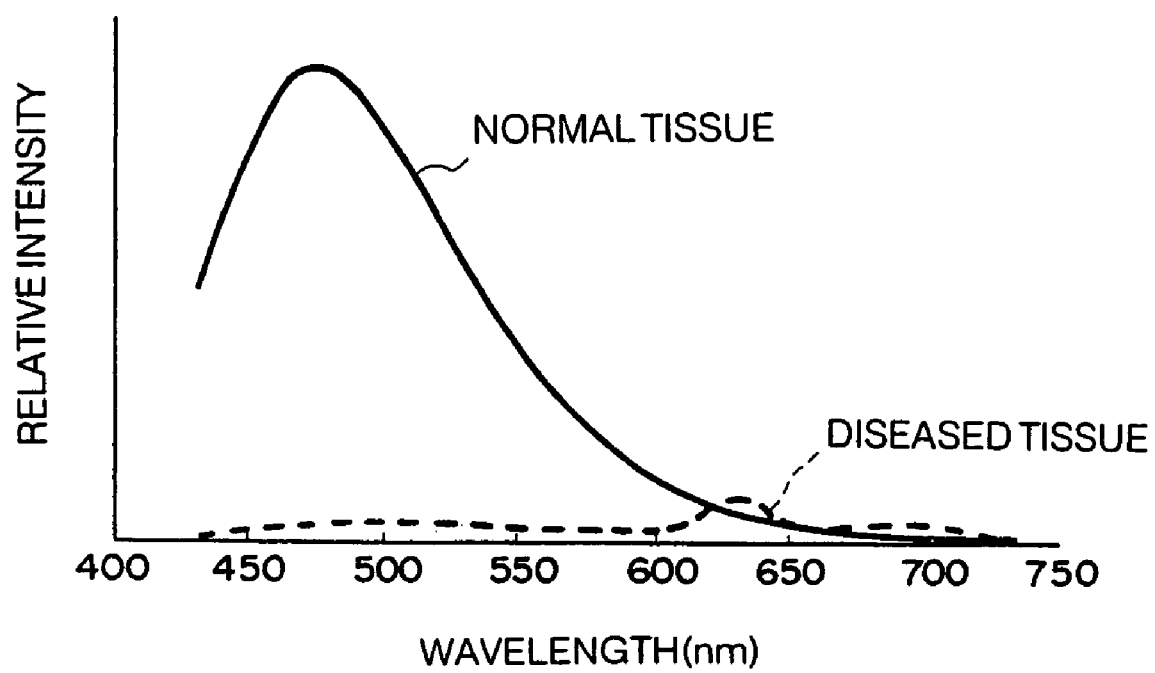
FIG. 26 is a drawing illustrating the intensity distributions of the fluorescent light spectra of a tissue in the diseased state and of a tissue in the normal state.

Additionally, according to the above-described thirteenth and fourteenth embodiments, the luminosity image data V has been formed, based on the wide band fluorescent image data WS', which has been multiplied by the gain rg, by the luminosity image data forming means 422; however, according to the sixteenth embodiment shown in FIG. 25, the luminosity image data V may also be formed based on the wide band fluorescent image data WS, which has not yet been multiplied by the gain rg. Note that needless to say, the luminosity image data V can also be formed based on the narrow band fluorescent image data NS or the reflectance image data RS, which has not yet been multiplied by the gain rg. In this case, it is preferable that it be possible to switch the image data, based upon which the luminosity image data is to be formed, between that which has not yet been multiplied by the gain rg and that which has been multiplied by the gain rg.

Note that for cases in which the luminosity image data V has been formed, based on the wide band fluorescent image data WS', which has been multiplied by the gain rg, because the gain changes by a large amount if the distance between the target subject 50 and the distal end of the endoscope insertion portion 100 changes a large amount, the brightness of the displayed composite image is also changed by a large amount. Therefore, by forming the luminosity image data V based on the wide band fluorescent image data WS, which has not yet been multiplied by the gain rg, a large change in the brightness of the composite image can be prevented.

Note that according to the thirteenth through the sixteenth embodiments, although the hue image H (a uniform saturation) has been computed, these embodiments are not limited thereto: an image corresponding to the the X,Y components of an XYZ color space; the ab components of a Lab color space; the uv components of a Luv color space; the a*b* components of a uniform La*b* color space; the u*v* components of a uniform Lu*v* color space; etc., can also be computed.

Further, according to the first through the sixteenth embodiments described above, the statistical quantity computed by the statistical quantity computing means 403, 803 can be computed based on fluorescent image or the reflectance image obtained in the frame preceding the frame in real time frame, instead of a single frame in real time frame of the fluorescent image or the reflectance image.

Still further, according to the first through the sixteenth embodiments, a standard image obtaining element 107 has been disposed in the distal end of the endoscope insertion portion 100; however, by utilizing an image fiber, the standard image obtaining element 107 can be disposed within the interior of the image data processing portion of the endoscope. Further, the standard image fiber, the fluorescent image fiber and the image obtaining element can be provided in the form of a common unit. In this case, the optical transmitting filter can be provided with a filter for obtaining standard images. Still further, by providing the image obtaining element with an on-chip mosaic filter that has a functionality equivalent to that of the filter for obtaining standard images with which the optical transmitting filter has been provided, the standard image obtaining element and the fluorescent image obtaining element can be provided in the distal end portion of the endoscope insertion portion.

In addition, according to the composite image display method, a standard image display monitor 601 and a composite image display monitor 602 have been provided separately; however, both said types of images can be displayed on a single monitor. In this case, the switching between the display of the standard image and the composite image can be automatically controlled in a temporal series manner by the control computer, by use of an appropriate switching means to be operated by the operator, or by a desired switching configuration. Further, the standard image and the composite image may be superposed and displayed.

Additionally, the image fiber 103 can be provided as a composite glass fiber instead of a quartz glass fiber. In this case, because a composite glass fiber emits fluorescent light when an excitation light enters therein, an excitation light cutoff filter 302 must be provided between the focusing lens 106 and the fluorescent light entry end of the image fiber 103. By using a composite glass fiber instead of a quartz glass fiber, the cost can be reduced.

Note that according to the first through the sixteenth embodiments, the computational process of the image computing unit 400 are not limited to being performed on each pixel unit; the processes can be performed on the pixel units corresponding to the binning process of the high sensitivity fluorescence image obtaining element, or on an arbitrary vertical by horizontal (n×m) block of pixels selected by the operator.

Further, any light source that emits light having a wavelength in the 400-420 nm wavelength band can be selected as the excitation light source.

Still further, according to the first through the sixteenth embodiments, the excitation light source and the white light source have been provided separately; however, by employing an appropriate optical filter, a common light source can be employed.

What is claimed is:

1. A fluorescence image display apparatus comprising:
    a fluorescence image obtaining means for irradiating a target subject with an excitation light and obtaining two fluorescence image data, each formed of fluorescent light of a mutually different wavelength band, based on a fluorescent light intensity emitted from the target subject upon the irradiation thereof by the excitation light,
    a reflectance image obtaining means for irradiating a target subject with a reference light and obtaining a reflectance image data, based on the intensity of the reference light reflected from the target subject upon the irradiation thereof by the reference light,
    a gain computing means for computing, based on a statistical quantity of said reflectance image data, a gain that said two fluorescence image data are to be multiplied by,
    a multiplying means for multiplying said two fluorescence image data and the reflectance image data by said gain to obtain two multiplied fluorescence image data and a multiplied reflectance data,
    a difference computing means for computing the difference data between the multiplied reflectance image data and either of the two multiplied fluorescence image data,
    an image forming means for forming, based on said difference data and the multiplied fluorescence image data that was not used in the computation of said difference data, a pseudo color image data representing a pseudo color image reflecting the tissue state of the target subject, and
    an image display means for displaying said pseudo color image.

2. A fluorescence image display apparatus as defined in claim 1, wherein
    said image forming means comprises a means for forming the pseudo color image, based on an additive color mixture method, from both of the multiplied fluorescence image data.

3. A fluorescence image display apparatus as defined in claim 1, wherein the image forming means comprises:
    a color image forming means for forming a color added and mixed image data, based on an additive color mixture method, from the difference data and the multiplied fluorescence image data, and a color image data, based on said color added and mixed image data, representing the chromatic components of the color added and mixed image represented by said color added and mixed image data,
    a luminosity image forming means for assigning a luminosity display gradation to the pixel values of the multiplied reflectance image represented by the multiplied reflectance image data or the pixel values of the multiplied fluorescence image represented by either of the two multiplied fluorescence image data to form a luminosity image data representing a luminosity image, and a composite image forming means for combining the color image data and the luminosity image data to form a pseudo color image data.

4. A fluorescence image display apparatus as defined in any of the claim 1, 2, or 3, further comprising:

a dynamic range expanding means for expanding, based on the statistical quantity, at least one of the dynamic range of the reflectance image data and both of the multiplied fluorescence image data so that the dynamic range thereof spans substantially the entirety of the dynamic range of the display means, wherein said image forming means comprises a means for obtaining a reverse fluorescence image data by inverting the light intensity of either of the multiplied fluorescence image data, and forming a pseudo color image based on this reverse fluorescence image data and the other multiplied fluorescence image data of the two multiplied fluorescence image data.

5. A fluorescence image obtaining apparatus as defined in any of the claims 1, 2, or 3, further including an illuminating device and a readout device, and wherein a portion or the entirety of one or more of the illuminating device, the image obtaining means, and the readout device is part of an endoscope provided with an insertion portion to be inserted into a body cavity of a patient, wherein said image forming means comprises a means for obtaining a reverse fluorescence image data by inverting the light intensity of either of the multiplied fluorescence image data, and forming a pseudo color image based on this reverse fluorescence image data and the other multiplied fluorescence image data of the two multiplied fluorescence image data.

6. A fluorescence image display apparatus comprising:

a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on a statistical quantity of said reflectance image data, a gain that said two fluorescence image data are to be multiplied by, a multiplying means for multiplying said two fluorescence image data by said gain to obtain two multiplied fluorescence image data, an image forming means for forming, based on said two multiplied fluorescence image data, a pseudo color image data representing a pseudo color image reflecting the tissue state of the target subject, and an image display means for displaying said pseudo color image, wherein said image forming means comprises a means for obtaining a reverse fluorescence image data by inverting the light intensity of either of the multiplied fluorescence image data, and forming a pseudo color image based on this reverse fluorescence image data and the other multiplied fluorescence image data of the two multiplied fluorescence image data.

7. A fluorescence image display apparatus comprising:

a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on a statistical quantity of said reflectance image data, a gain that said two fluorescence image data are to be multiplied by, a multiplying means for multiplying said two fluorescence image data by said gain to obtain two multiplied fluorescence image data, an image forming means for forming, based on said two multiplied fluorescence image data, a pseudo color image data representing a pseudo color image reflecting the tissue state of the target subject, an image display means for displaying said pseudo color image, and a dynamic range expanding means for expanding, based on the statistical quantity, at least one of the dynamic range of the reflectance image data and both of the multiplied fluorescence image data so that the dynamic range thereof spans substantially the entirety of the dynamic range of the display means, wherein said image forming means comprises a means for obtaining a reverse fluorescence image data by inverting the light intensity of either of the multiplied fluorescence image data, and forming a pseudo color image based on this reverse fluorescence image data and the other multiplied fluorescence image data of the two multiplied fluorescence image data.

8. A fluorescence image display apparatus comprising:

a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on a statistical quantity of said reflectance image data, a gain that said two fluorescence image data are to be multiplied by, a multiplying means for multiplying said two fluorescence image data by said gain to obtain two multiplied fluorescence image data, an image forming means for forming, based on said two multiplied fluorescence image data, a pseudo color image data representing a pseudo color image reflecting the tissue state of the target subject, an image display means for displaying said pseudo color image, and an illuminating device and a readout device, and wherein a portion or the entirety of one or more of the illuminating device, the image obtaining means, and the readout device is part of an endoscope provided with an insertion portion to be inserted into a body cavity of a patient; wherein said image forming means comprises a means for obtaining a reverse fluorescence image data by inverting the light intensity of either of the multiplied fluorescence image data, and forming a pseudo color image based on this reverse fluorescence image data and the other multiplied fluorescence image data of the two multiplied fluorescence image data.

9. A fluorescence image display apparatus comprising:

a fluorescence image obtaining means for irradiating a target subject with an excitation light and obtaining two fluorescence image data, each formed of fluorescent light of a mutually different wavelength band, based on the fluorescent light intensity emitted from the target subject upon the irradiation thereof by the excitation light, a reflectance image obtaining means for irradiating a target subject with a reference light and obtaining a reflectance image data, based on the intensity of the reference light reflected from the target subject upon the irradiation thereof by the reference light, a gain computing means for computing, based on a statistical quantity of said reflectance image data, a gain that said two fluorescence image data are to be multiplied by, a multiplying means for multiplying said two fluorescence image data by said gain to obtain two multiplied fluorescence image data, an image forming means for forming, based on said two multiplied fluorescence image data, a pseudo color image data representing a pseudo color image reflecting the tissue state of the target subject, and an image display means for displaying said pseudo color image, wherein said image forming means comprises a means for obtaining a reverse fluorescence image data by inverting the light intensity of the multiplied fluorescence image data related to a narrow band, and forming a pseudo color image based on this reverse fluorescence image data and the other multiplied fluorescence image data of the two multiplied fluorescence image data.

* * * * *